US007253191B2

(12) United States Patent
Laufer et al.

(10) Patent No.: US 7,253,191 B2
(45) Date of Patent: Aug. 7, 2007

(54) 2-THIO-SUBSTITUTED IMIDAZOLE DERIVATIVES AND THE USE THEREOF IN THE PHARMACEUTICAL INDUSTRY

(75) Inventors: Stefan Laufer, Blaubeuren (DE); Dunja Kotschenreuther, Ulm (DE); Philipp Merckle, Blaubeuren-Weiler (DE); Karola Tollmann, Brechen (DE); Hans-Guenter Striegel, Blaustein (DE)

(73) Assignee: Merckle GmbH, Ulm (DE)

( * ) Notice: Subject to any disclaimer, the term of this patent is extended or adjusted under 35 U.S.C. 154(b) by 475 days.

(21) Appl. No.: 10/467,064

(22) PCT Filed: Feb. 19, 2002

(86) PCT No.: PCT/EP02/01746

§ 371 (c)(1),
(2), (4) Date: Jan. 28, 2004

(87) PCT Pub. No.: WO02/066458

PCT Pub. Date: Aug. 29, 2002

(65) Prior Publication Data

US 2004/0116416 A1 Jun. 17, 2004

(30) Foreign Application Priority Data

Feb. 19, 2001 (DE) ................. 101 07 683

(51) Int. Cl.
*A61K 31/44* (2006.01)
*C07D 401/04* (2006.01)
(52) U.S. Cl. ................ 514/341; 546/268.1; 546/272.7; 546/274.1; 514/336; 514/385; 514/397; 514/398
(58) Field of Classification Search ............ 546/268.1, 546/272.7, 274.1; 548/300.1, 311.1, 319.7; 514/336, 341, 385, 397, 398
See application file for complete search history.

(56) References Cited

U.S. PATENT DOCUMENTS

| 4,190,666 A | 2/1980 | Cherkofsky et al. |
| 4,402,960 A | 9/1983 | Niedballa et al. |
| 4,461,770 A | 7/1984 | Ferrini et al. |
| 4,528,298 A | 7/1985 | Niedballa et al. |
| 4,584,310 A | 4/1986 | Ferrini et al. |
| 4,585,771 A | 4/1986 | Klose et al. |
| 4,608,382 A * | 8/1986 | Ferrini et al. ............... 514/341 |
| 5,364,875 A | 11/1994 | Wilde |
| 6,040,320 A | 3/2000 | Beers et al. |
| 6,432,988 B1 | 8/2002 | Laufer et al. |
| 2004/0116416 A1 | 6/2004 | Laufer et al. |

FOREIGN PATENT DOCUMENTS

| CN | 1083473 A | 3/1994 |
| DE | 28 23 197 | 11/1979 |
| DE | 35 04 678 | 8/1986 |
| EP | 0 004 648 | 10/1979 |
| EP | 0 005 545 | 11/1979 |
| EP | 0 236 628 | 9/1987 |
| EP | 0 327 445 | 8/1989 |
| GB | 1 155 580 | 6/1969 |
| GB | 1 564 184 | 4/1980 |
| JP | 01 40467 | 2/1989 |
| WO | 91/10662 | 7/1991 |
| WO | 93 14081 | 7/1993 |
| WO | 95/00501 | 1/1995 |
| WO | WO 95/03297 | 2/1995 |
| WO | 96/03387 | 2/1996 |
| WO | 99 03837 | 1/1999 |
| WO | 00/17192 | 3/2000 |

OTHER PUBLICATIONS

Ferrini et al (1980): STN International HCAPLUS database, Columbus (OH), accession No. 1980: 76510.*
J. Med. Chem. vol. 39, pp. 3929-3937 1996.
Acta Chim. 61(1)69-77 1969(English Abstract Only).
Journal f.prakt. Chernie., Band 314, pp. 785-792 1972.
Grzegorz Mloston et al.: "Trapping of a thiocarbonyl ylide with imidazolethiones, pyrimidinethlone, and thioamides" Helvetica Chimica Acta., vol. 82, No. 2, pp. 290-296 1990.
Grzegorz Mloston et al.: "First examples of reactions of azole N-oxides with thioketones: a novel type of sulfur-transfer reaction" Helvetical Chimica Acta., vol. 81, No. 9, pp. 1585-1595, 1998.
Chemical Abstracts, vol. 117, No. 17, Oct. 26, 1992 abstract No. 166037b Beach, Dorothy C. et al.: "Inhibition of peroxidation by iron(III) and ascorbate".
U.S. Appl. No. 10/524,486, filed Feb. 14, 2005, Laufer et al.
U.S. Appl. No. 10/524,839, filed Feb. 17, 2005, Laufer et al.

* cited by examiner

*Primary Examiner*—Golam M. M. Shameem
(74) *Attorney, Agent, or Firm*—Oblon, Spivak, McClelland, Maier & Neustadt, P.C.

(57) ABSTRACT

The invention relates to 2-thio-substituted imidazole derivatives of the formula I

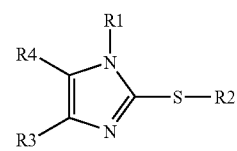

in which the radicals $R_1$, $R_2$, $R_3$ and $R_4$ are as defined in the description. The compounds according to the invention have immunomodulating and/or cytokine-release-inhibiting action and are therefore suitable for treating disorders associated with a disturbed immune system.

12 Claims, No Drawings

2-THIO-SUBSTITUTED IMIDAZOLE DERIVATIVES AND THE USE THEREOF IN THE PHARMACEUTICAL INDUSTRY

The present invention relates to 2-thio-substituted imidazole derivatives having immunomodulating and cytokine-release-inhibiting action, to pharmaceutical compositions comprising these compounds and to their use in pharmacy.

Pharmacologically active imidazole compounds with antiinflammatory activity are already known.

Thus, inter alia, compounds having 4,5-di(hetero)arylimidazole moieties have been examined more closely, and various pharmaceutical actions thereof have been described. Also known are compounds which are substituted in the 2-position.

U.S. Pat. No. 4,585,771 discloses 4,5-diphenylimidazole derivatives which are substituted in the 2-position by a pyrrolyl, indolyl, imidazolyl or thiazolyl radical and which have antiinflammatory and antiallergic activity.

U.S. Pat. Nos. 4,528,298 and 4,402,960 describe 4,5-di(hetero)arylimidazole derivatives which are substituted in the 2-position via a thio, sulfinyl or sulfonyl group by a phenyl, pyridyl, N-oxypyridyl, pyrimidyl, thiazolyl or thienyl radical and which have antiinflammatory and antiallergic activity.

U.S. Pat. Nos. 4,461,770 and 4,584,310 describe 4-(5-aryl)5-(4-heteroaryl)imidazole derivatives which are substituted in the 2-position via a thio, sulfinyl or sulfonyl group by a substituted or unsubstituted aliphatic hydrocarbon and which, inter alia, have antiinflammatory action.

DE 198 42 833 relates to 4-heteroaryl-5-phenylimidazole derivatives which are substituted in the 2-position by a phenylalkylthio group. These compounds act as antiinflammatories and inhibitors of cytokine release. WO 99/03837 and WO 93/14081 describe 2-substituted imidazoles which inhibit the synthesis of a number of inflammatory cytokines. The compounds described in WO 93/14081 have in the 2-position, attached via a sulfur atom, a phosphorus-containing substituent or an aryl or heteroaryl substituent. WO 91/10662 describes imidazole derivatives which inhibit the acyl-CoA: cholesterol 0-acyl transferase and binding of thromboxane $TxA_2$. WO 95/00501 describes imidazole derivatives which can be used as cyclooxygenase inhibitors. The imidazole derivatives described in DE 28 23 197 A have antiinflammatory, antiallergic and immunostimulating action.

J. Med. Chem. 1996, 39, 3927-37 describes compounds having 5-lipoxygenase- and cyclooxygenase-inhibiting action, 2-(4-methylsulfinylphenyl)-4-(4-fluorophenyl-5-(pyrid-4-yl)imidazole also having cytokine-inhibiting action.

It has been found that the known compounds are unstable and difficult to process, or that their efficacy is low.

In spite of the fact that numerous compounds are known, there is therefore still a need for compounds having antiinflammatory action which inhibit cytokine release.

It is an object of the invention to provide such compounds.

Surprisingly, it has now been found that certain 2-substituted imidazole derivatives provide stable compounds which are readily processible and which have high immunomodulating and/or cytokine-release-inhibiting activity.

Accordingly, the present invention provides 2-thio-substituted imidazole derivatives of the formula I

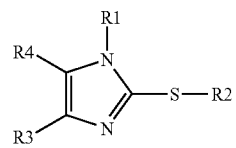

where $R^1$ is selected from the group consisting of:
$C_1$-$C_6$-alkyl which is unsubstituted or substituted by one or two hydroxyl or $C_1$-$C_4$-alkoxy groups or by a nonaromatic heterocyclic radical having 5 or 6 ring atoms and 1 or 2 heteroatoms independently of one another selected from the group consisting of N, O and S, $C_2$-$C_6$-alkenyl, $C_3$-$C_6$-cycloalkyl, aryl which is unsubstituted or substituted by one or more halogen atoms or by a $C_1$-$C_4$-alkylsulfanyl group, amino-$C_1$-$C_4$-alkyl, where the amino group is unsubstituted or substituted by one or two $C_1$-$C_4$-alkyl groups, aminoaryl, where the amino group is unsubstituted or substituted by one or two $C_1$-$C_4$-alkyl groups, aryl-$C_1$-$C_4$-alkyl or an aromatic or nonaromatic heterocyclic radical having 5 or 6 ring atoms and 1 or 2 heteroatoms independently of one another selected from the group consisting of N, O and S, which heterocyclic radical is unsubstituted or substituted by 1, 2, 3 or 4 $C_1$-$C_4$-alkyl groups, an aryl or aryl-$C_1$-$C_4$-alkyl group, $R^2$ is selected from the group consisting of:

H;

$C_1$-$C_6$-alkyl, phenyl-$C_1$-$C_4$-alkyl, where the phenyl group may have one or two substituents independently of one another selected from the group consisting of $C_1$-$C_4$-alkyl, halogen, $C_1$-$C_4$-alkylsulfanyl, $C_1$-$C_4$-alkylsulfinyl and $C_1$-$C_4$-alkylsulfonyl, $C_2$-$C_6$-alkenyl, $C_2$-$C_6$-alkenyl which is substituted by one or two halogen atoms and/or phenyl groups, where the phenyl group may independently be substituted by one or two $C_1$-$C_4$-alkyl or halogen atoms, $C_2$-$C_6$-alkynyl, $C_2$-$C_6$-alkynyl which is substituted by a phenyl group which may be unsubstituted or substituted by one or two $C_1$-$C_4$-alkyl or halogen atoms, $C_1$-$C_6$-alkyl which is substituted by a nonaromatic heterocyclic radical having 5 or 6 ring atoms and 1 or 2 heteroatoms independently of one another selected from the group consisting of N, O and S, $C_1$-$C_4$-alkylsulfanyl, $C_1$-$C_4$-alkylsulfinyl or $C_1$-$C_4$-alkylsulfonyl, phenyl or phenyl which has one or two substituents independently of one another selected from the group consisting of $C_1$-$C_4$-alkyl, halogen, $C_1$-$C_4$-alkylsulfanyl, $C_1$-$C_4$-alkylsulfinyl and $C_1$-$C_4$-alkylsulfonyl, or R$^1$ and R$^2$ together are —CH$_2$CH$_2$— or —CH$_2$CH$_2$CH$_2$—, one of the radicals R$^3$ and R$^4$ is C$_1$-C$_6$-alkyl or an aromatic heterocyclic radical having 5 or 6 ring atoms and 1 or 2 heteroatoms independently of one another selected from the group consisting of N, O and S, where the aromatic heterocyclic radical may have 1 or 2 substituents independently of one another selected from the group consisting of C$_1$-C$_6$-alkyl, amino, C$_1$-C$_4$-alkylamino, di-C$_1$-C$_4$-alkylamino, phenyl-C$_1$-C$_4$-alkylamino and R$^5$CONR$^6$—, where R$^5$ is C$_1$-C$_4$-alkyl, phenyl, which may have one or two substituents independently of one another selected from the group consisting of C$_1$-C$_4$-alkyl, C$_1$-C$_4$-alkoxy and halogen, or C$_3$-C$_6$-cycloalkyl and R$^6$ is H, C$_1$-C$_4$-alkyl or benzyl, and the second of the radicals R$^3$ and R$^4$ is C$_1$-C$_6$-alkyl or aryl which is unsubstituted or substituted by a halogen atom, where only one of the radicals R$^3$ and R$^4$ may be C$_1$-C$_6$-alkyl, with the proviso that, if R$^1$ represents aryl-C$_1$-C$_5$-alkyl or amino-C$_1$-C$_6$-alkyl, R$^2$ represents alkylsulfonyl- or alkylsulfinylaryl-C$_1$-C$_5$-alkyl, their optical isomers and physiologically acceptable salts.

Preference is given to compounds of the formula I in which R$^1$ is C$_1$-C$_6$-alkyl which is unsubstituted or substituted by one or two hydroxyl groups or a nonaromatic heterocyclic radical, C$_2$-C$_6$-alkenyl, C$_3$-C$_6$-cycloalkyl, aryl which is unsubstituted or substituted by one or more halogen atoms or a C$_1$-C$_4$-alkylsulfanyl group, amino-C$_1$-C$_4$-alkyl, where the amino group is unsubstituted or substituted by one or two C$_1$-C$_4$-alkyl groups, aminoaryl, where the amino group is unsubstituted or substituted by one or two C$_1$-C$_4$-alkyl groups, aryl-C$_1$-C$_4$-alkyl or an aromatic or nonaromatic heterocyclic radical having 5 or 6 ring atoms and 1 or 2 heteroatoms independently of one another selected from the group consisting of N, O and S, which heterocyclic radical is unsubstituted or substituted by 1, 2, 3 or 4 C$_1$-C$_4$-alkyl groups, an aryl or aryl-C$_1$-C$_4$-alkyl group, R$^2$ is H, C$_1$-C$_6$-alkyl, phenyl-C$_1$-C$_4$-alkyl, where the phenyl group may have one or two substituents independently of one another selected from the group consisting of C$_1$-C$_4$-alkyl, halogen, C$_1$-C$_4$-alkylsulfanyl, C$_1$-C$_4$-alkylsulfinyl and C$_1$-C$_4$-alkylsulfonyl, C$_2$-C$_6$-alkenyl, C$_2$-C$_6$-alkenyl which is substituted by one or two halogen atoms and/or phenyl groups, where the phenyl group may independently be substituted by one or two C$_1$-C$_4$-alkyl or halogen atoms, C$_2$-C$_6$-alkynyl, C$_2$-C$_6$-alkynyl which is substituted by a phenyl group which may be unsubstituted or substituted by one or two C$_1$-C$_4$-alkyl or halogen atoms, C$_1$-C$_6$-alkyl which is substituted by a nonaromatic heterocyclic radical having 5 or 6 ring atoms and 1 or 2 heteroatoms independently of one another selected from the group consisting of N, O and S, one of the radicals R$^3$ and R$^4$ is C$_1$-C$_6$-alkyl or an aromatic heterocyclic radical having 5 or 6 ring atoms and 1 or 2 heteroatoms independently of one another selected from the group consisting of N, O and S, where the aromatic heterocyclic radical may have 1 or 2 substituents independently of one another selected from the group consisting of C$_1$-C$_6$-alkyl, amino, C$_1$-C$_4$-alkylamino, di-C$_1$-C$_4$-alkylamino, phenyl-C$_1$-C$_4$-alkylamino, R$^5$CONR$^6$—, where R$^5$ is C$_1$-C$_4$-alkyl, phenyl which may have one or two substituents independently of one another selected from the group consisting of C$_1$-C$_4$-alkyl, C$_1$-C$_4$-alkoxy and halogen, or C$_3$-C$_6$-cycloalkyl, and R$^6$ is H, C$_1$-C$_4$-alkyl or benzyl, and the second of the radicals R$^3$ and R$^4$ is C$_1$-C$_6$-alkyl or aryl which is unsubstituted or substituted by a halogen atom, where only one of the radicals R$^3$ and R$^4$ may be C$_1$-C$_6$-alkyl.

If the compounds according to the invention have centers of asymmetry, the scope of the invention includes both racemates and optical isomers (enantiomers, diastereomers).

The term "alkyl" (also in combination with other groups, such as phenylalkyl, alkylsulfonyl, etc.) embraces straight-chain and branched alkyl groups having preferably 1 to 6 or 1 to 4 carbon atoms, such as methyl, ethyl, n- and i-propyl, n-, i- and t-butyl, sec-butyl, n-pentyl and n-hexyl.

The term "aryl" embraces aromatic ring systems, such as phenyl or naphthyl.

The term "halogen" represents a fluorine, chlorine, bromine or iodine atom, in particular a fluorine or chlorine atom.

C$_3$-C$_6$-Cycloalkyl groups are cyclopropyl, cyclobutyl and, in particular, cyclopentyl and cyclohexyl.

Nonaromatic heterocyclic radicals can be saturated or unsaturated. Preference is given to piperidinyl, piperazinyl, pyranyl, morpholinyl or pyrrolidinyl, where the piperidinyl radical may be substituted by 1, 2, 3 or 4 C$_1$-C$_4$-alkyl groups, in particular methyl groups.

Preferred aromatic heterocyclic radicals are pyridyl, in particular 3- or 4-pyridyl, pyrimidinyl, pyrrolyl, imidazolyl, oxazolyl, isoxazolyl, furyl, thienyl or thiazolyl. The heterocyclic radical, in particular the pyridyl radical, may be substituted as mentioned above. The pyridyl radical is substituted in particular in the 2-position.

Phenyl-C$_1$-C$_4$-alkyl is in particular benzyl or phenylethyl.

Preference is given to compounds of the formula I in which one of the radicals R$^3$ and R$^4$ is C$_1$-C$_4$-alkyl or a halogen-substituted phenyl and the second of the radicals R$^3$ and R$^4$ is C$_1$-C$_4$-alkyl or pyridyl or substituted pyridyl, with the proviso, that the two radicals are not both C$_1$-C$_4$-alkyl.

Preference is furthermore given to compounds of the formula I where R$^3$ is halogen-substituted, in particular 4-substituted, phenyl and R$^4$ is unsubstituted or substituted pyridyl, in particular 4-pyridyl or substituted 4-pyridyl.

According to a particularly preferred embodiment, the radical R$^3$ in the formula I is 4-fluorophenyl and R$^4$ is 4-pyridyl or substituted pyridyl.

If R$^1$ is C$_1$-C$_6$-alkyl which is substituted by a nonaromatic heterocyclic radical, this radical preferably contains at least one nitrogen atom, and the attachment to the alkyl group is preferably via the nitrogen atom.

If R$^1$ is an aromatic or nonaromatic heterocyclic radical, this is preferably attached to the imidazole group via a carbon atom.

R$^1$ is preferably C$_1$-C$_3$-alkyl, C$_3$-C$_6$-cycloalkyl, in particular cyclopropyl, or a saturated heterocyclic radical having one or two nitrogen atoms, in particular piperidinyl or 2,2,6,6-tetramethylpiperidinyl. With particular preference, the piperidinyl or 2,2,6,6-tetramethylpiperidinyl radical is attached in the 4-position to the nitrogen atom of the imidazole.

$R^2$ is preferably $C_1$-$C_3$-alkyl (methyl, ethyl, n-propyl or i-propyl) or phenyl-$C_1$-$C_4$-alkyl, in particular benzyl, which may be substituted as stated above. With particular preference, $R^2$ is $C_1$-$C_3$-alkyl or benzyl which is substituted by $C_1$-$C_4$-alkylsulfanyl, $C_1$-$C_4$-alkylsulfinyl or $C_1$-$C_4$-alkylsulfonyl, in particular in the 4-position.

Particular preference is given to compounds of the formula in which $R^4$ is pyridyl, in particular 4-pyridyl, which is substituted by amino, $C_1$-$C_4$-alkylamino or $R^5COR^6$-, where $R^5$ and $R^6$ are as defined above, $R^1$ is $C_1$-$C_3$-alkyl and $R^2$ is $C_1$-$C_3$-alkyl.

In the present case, the physiologically acceptable salts can be acid addition salts or base addition salts. For acid addition salts, inorganic acids, such as hydrochloric acid, sulfuric acid or phosphoric acid, or organic acids, such as tartaric acid, citric acid, maleic acid, fumaric acid, malic acid, mandelic acid, ascorbic acid, gluconic acid and the like, are used.

The compounds according to the invention where $R^2 \neq H$ are prepared in a two-step process. In the first step, initially a substituted imidazole-2-thione ($R^2$=H) is prepared. This is then reacted in the second step such that the desired substituent is introduced.

1) Preparation of the imidazole-2-thione

Two process variants are available for preparing the imidazole-2-thione. The two variants are illustrated in an exemplary manner using compounds in which $R^3$ is 4-fluorophenyl and $R^4$ is 4-pyridyl. Compounds having other radicals $R^3$ and $R^4$ can be prepared in an analogous manner.

Variant 1

The synthesis of the substituted imidazole-2-thiones is carried out according to the course of the reaction of scheme 1, using ethyl isonicotinate and 4-fluorophenyl-acetonitrile as starting materials.

The starting materials are converted in a condensation reaction with the aid of metallic sodium in an alcohol, for example ethanol, into 2-cyano-2-(4-fluorophenyl)-1-(4-pyridyl)ethanone (compound 1). The cyano group is then removed by hydrolysis, for example with hydrobromic acid, and decarboxylation, giving 2-(4-fluorophenyl)-1-(4-pyridyl)ethanone (compound 2). In the next step, compound 2 is nitrosated in the 2-position using, for example, nitrites, such as sodium nitrite or isoamyl nitrite.

This gives the compound of the formula (3), the oxime 2-(4-fluorophenyl)-1-(4-pyridyl)-α-hydroxyiminoethane.

Using this intermediate, cyclization giving an imidazole derivative of the formula (4), a substituted 5-(4-fluorophenyl)-4-(4-pyridyl)imidazole N-oxide which carries the substituent $R^1$ at the nitrogen atom in 3-position, is carried out by reaction with an imine of the general formula $H_2C=NR_1$, which is present as a 1,3,5-trisubstituted hexahydro-1,3,5-triazine, in an alcoholic solvent, such as ethanol, and at elevated temperature (50-90° C.). The imidazole N-oxide of the formula (4) is then reacted with 2,2,4,4-tetramethyl-3-thiocyclobutanone in a chlorinated solvent to give the corresponding 3-substituted 5-(4-fluorophenyl)-4-(4-pyridyl) imidazole-2-thione (compound 5; compound of the formula I where $R^2$=H).

Scheme 1:
Synthesis route for the thiones according to the invention (variant 1)

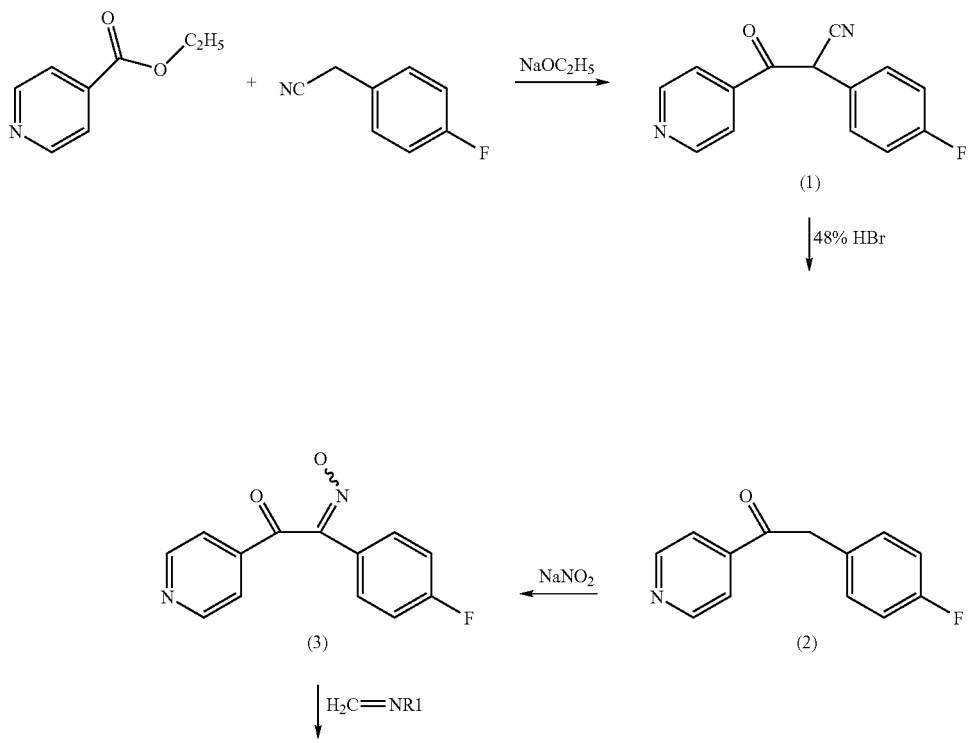

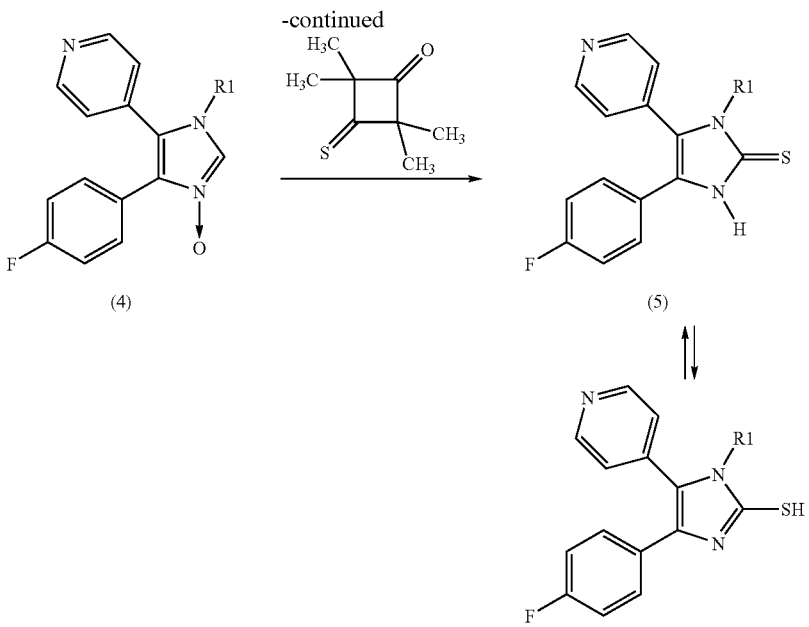

(4)　(5)

Variant 2

Initially, the oxime compound of the formula (3), 2-(4-fluorophenyl)-1-(4-pyridyl)-α-hydroxyiminoethane, is prepared as described in variant 1 (scheme 1, steps 1 to 3). Using this starting material, the synthesis of the substituted imidazole-2-thiones is carried out according to scheme 2.

2-(4-Fluorophenyl)-1-(4-pyridyl)-α-hydroxyiminoethane is, according to scheme 2, reacted with the selected amine of the general formula $NH_2$—$R_1$ and formaldehyde, giving, with ring closure, a compound of the formula (6), i.e. a 1-substituted 4-(4-fluorophenyl)-5-(4-pyridyl)imidazol-2-one. This is reacted with an excess of phosphorus oxychlo- Scheme 2:
Synthesis route for the thiones according to the invention (variant 2)

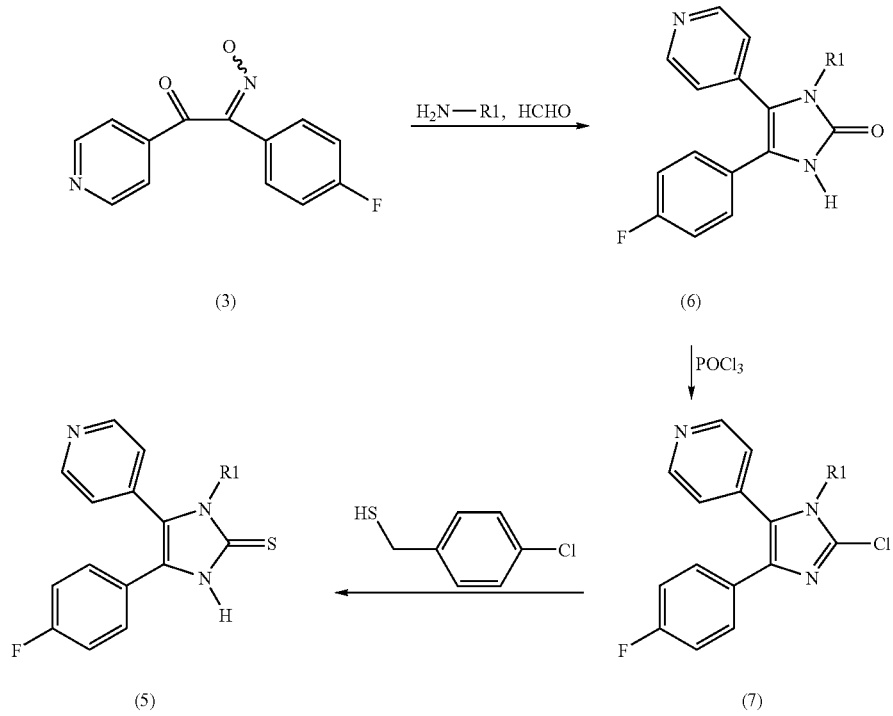

(3)　(6)

(5)　(7)

ride, resulting in a compound of the formula (7), i.e. a 1-substituted 4-(4-fluorophenyl)-5-(4-pyridyl)imidazole 2-chloride being formed. From this compound, the corresponding 1-substituted 4-(4-fluorophenyl)-5-(4-pyridyl)-imidazole-2-thione (compound 5) is obtained by reaction with 4-chlorobenzylthiol in a polar aprotic solvent and at elevated temperature (100-150° C.).

2) Preparation of the 2-thioimidazole compound

The thione compounds (5) obtained according to variant 1 or 2 are converted by substitution of the sulfur atom in the 2-position into the compounds of the formula I according to the invention where $R^2 \neq H$. The substitutions can be carried out in a known manner by a nucleophilic substitution reaction, as shown in an exemplary manner for some compounds in scheme 3. Here, compound 5 is reacted with $R^2$—X in an inert polar solvent, such as an alcohol. X is a readily exchangeable group, such as Hal, in particular Cl, Br, I, methylsulfonyl, tosyl etc.

2-Thioimidazole compounds in which the sulfur atom [lacuna] 2-position is substituted by a vinyl radical can be obtained by nucleophilic addition of compound 5 to a triple bond. To this end, 5 is reacted with a base, for example an alkali metal alkoxide in the corresponding alcohol, and then with an excess of the compound with the triple bond.

The corresponding bisaryl thioethers are prepared from the 3-substituted 2-chloro-4-(4-fluorophenyl)-5-(4-pyridyl) imidazole (compound 7 from scheme 2). The compounds (7) are reacted with two equivalents of the appropriate thiophenol in an aprotic solvent, such as dimethylformamide, giving compounds of the formula (12).

The corresponding regioisomeric compounds can be prepared in accordance with scheme (5). Starting with 1-(4-fluorophenyl)-2-(4-pyridyl)-α-hydroxyiminoethanone (obtained analogously to scheme 1), compounds of the formula 15 are obtained analogously to the process of scheme 1 by reaction with the appropriate imines. Compound (13) can be prepared by the process described in WO 93/14081.

Scheme 3:

3. Substitution of sulfur 3.1.

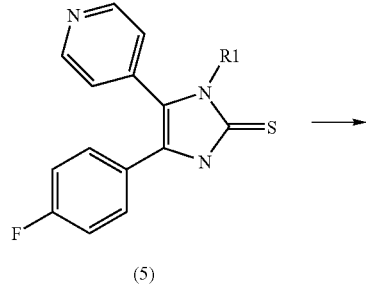

(5)

3.2.

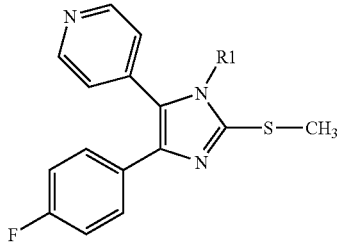

(8)

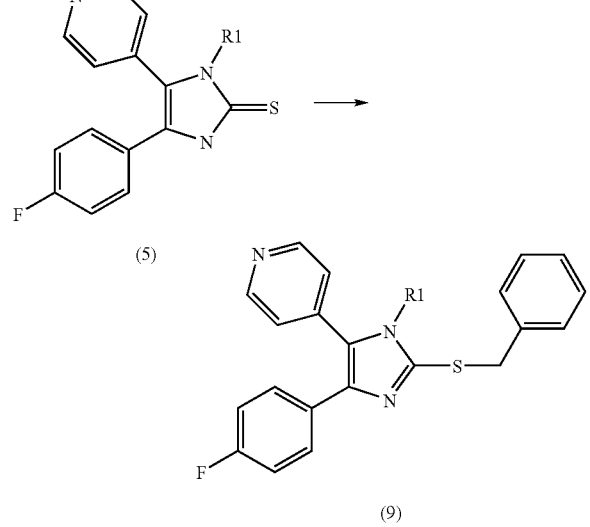

(9)

3.3.

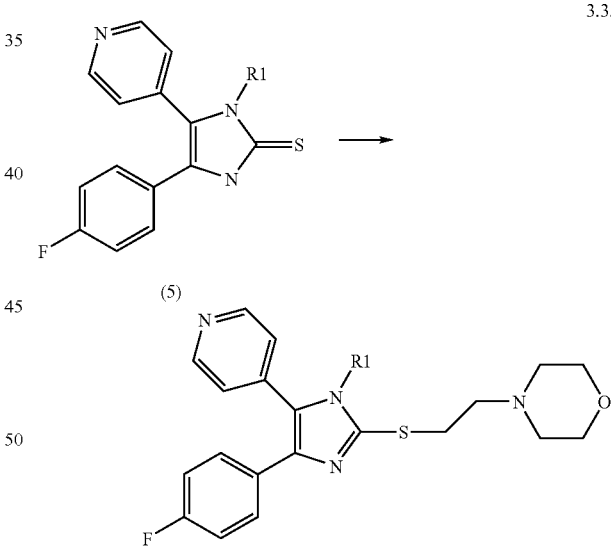

(10)

3.4.

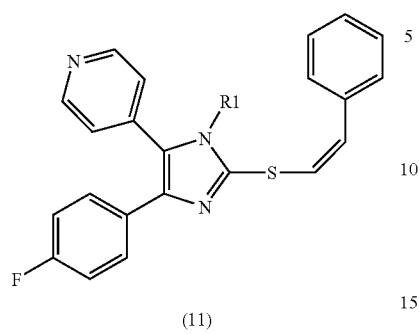
(11)
Scheme 4:
Bisaryl thioethers
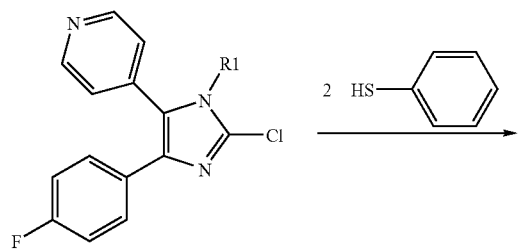
(7)
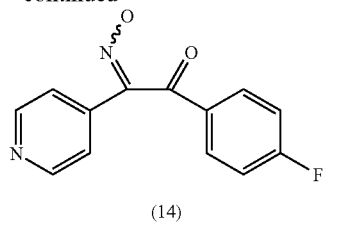
(14)
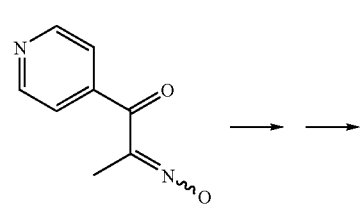
(15)
These compounds can be reacted further as described in scheme 3.
The imidazolethiols which carry a $C_1$-$C_4$-alkyl group in the 4-position are obtained from the corresponding α-hydroxyiminoethanones (compound 17/19 in scheme 6 below), analogously to schemes 1 and 2.
Scheme 6:
4-Methylimidazolethiones
6.1.
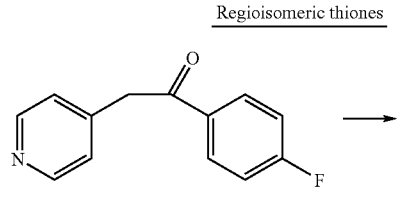
(17)
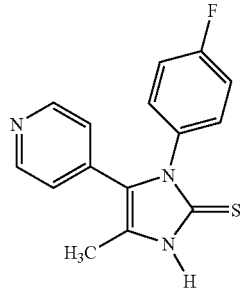
(18)
(12)
Scheme 5:
Regioisomeric thiones
(13)

-continued

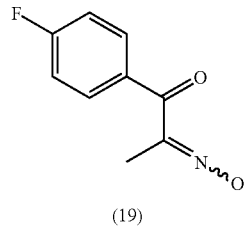

(19)

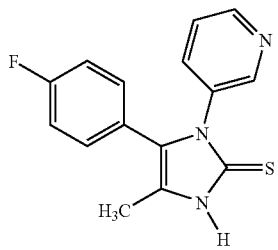

(20)

These compounds can be reacted further according to schemes 3 and 4. The corresponding regioisomeric compounds can be prepared analogously to scheme 5.

Compounds of the formula I which carry a $C_1$-$C_4$-alkyl-sulfanyl radical can be oxidized by known processes, using a suitable oxidizing agent, such as m-chloroperbenzoic acid, hydrogen peroxide, benzoyl peroxide, etc., to give the corresponding $C_1$-$C_4$-alkylsulfinyl or $C_1$-$C_4$-alkylsulfonyl compound, see scheme 7.

Scheme 7:

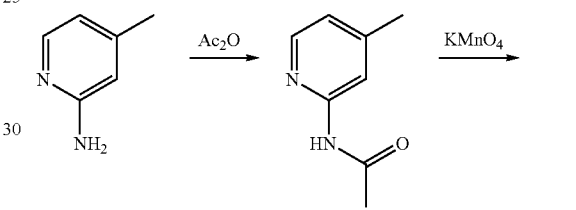

-continued

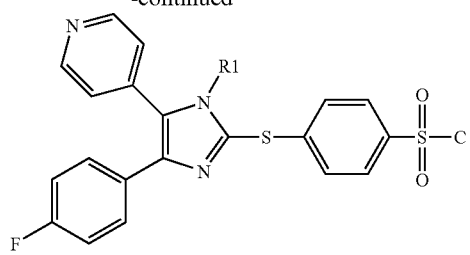

The preparation of the compounds in which $R^4$ is an amino- or amido-substituted heterocyclic radical, in particular a pyridyl radical, is carried out according to scheme 8, where the preparation is illustrated using 2-substituted 4-pyridine compounds as examples (compounds in which $R^4$ is an alkyl-substituted heterocyclic radical are prepared by the processes mentioned above using appropriately substituted starting materials):

Scheme 8:

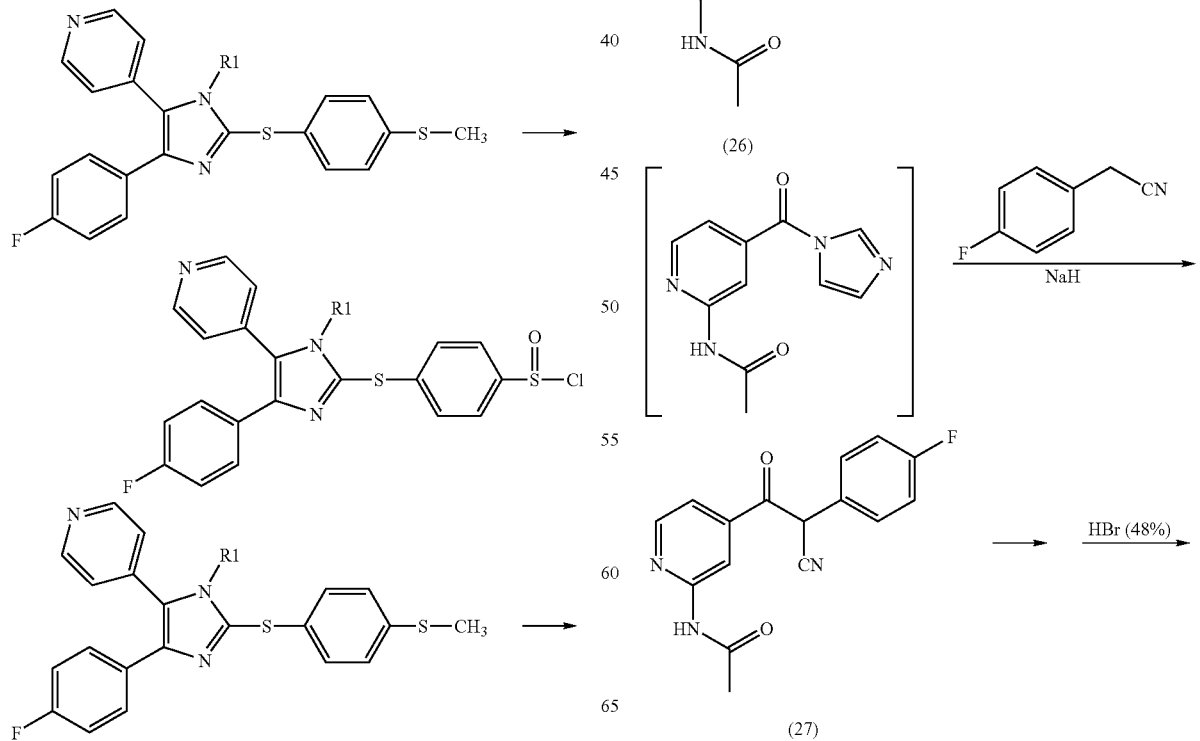

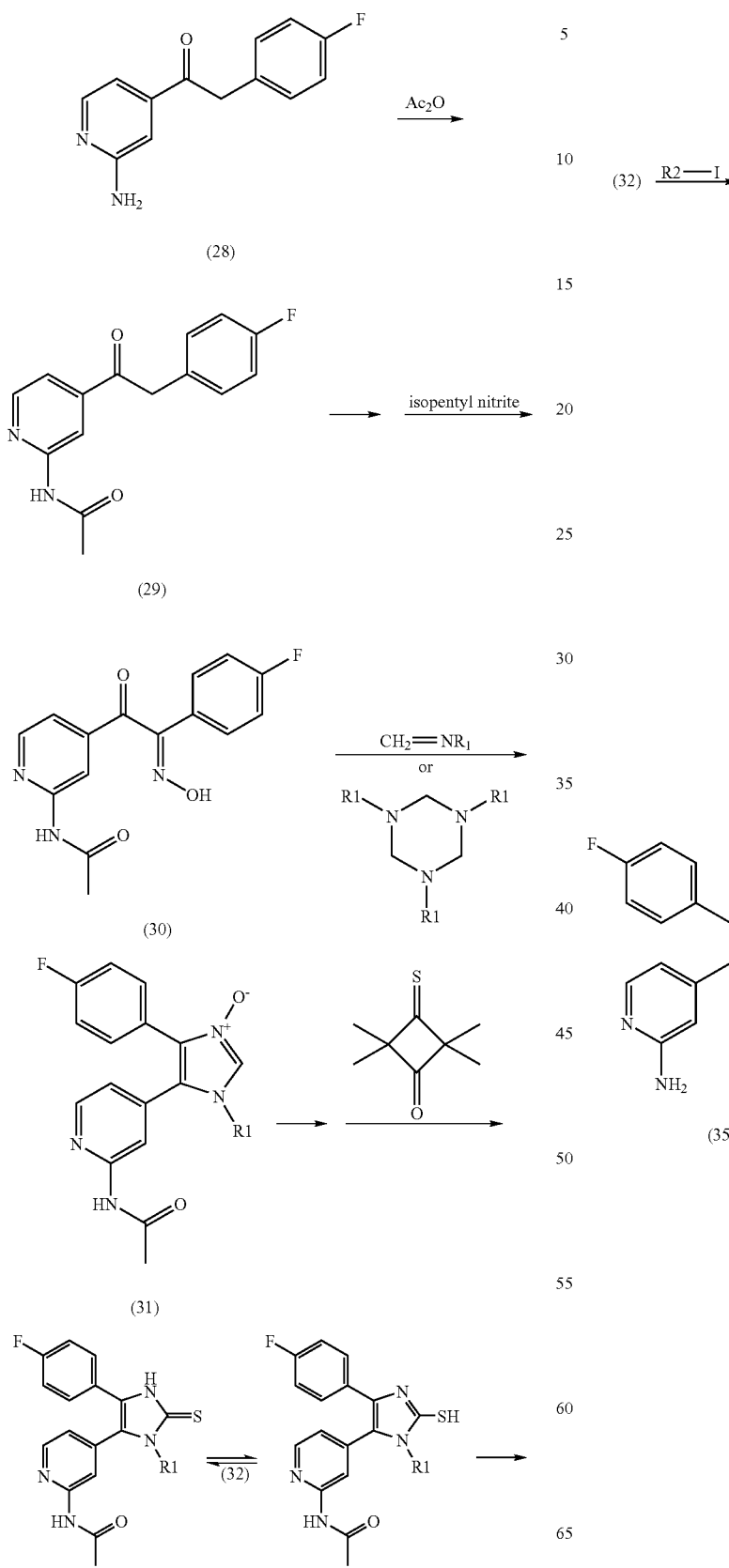
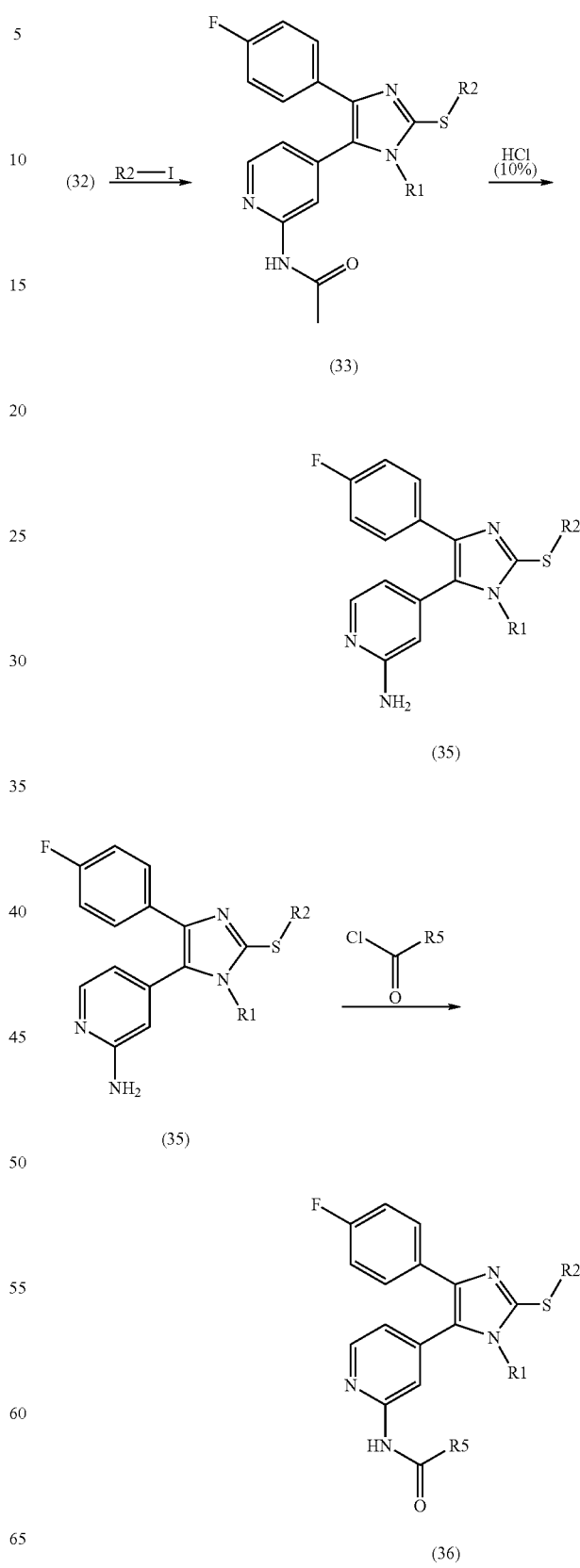

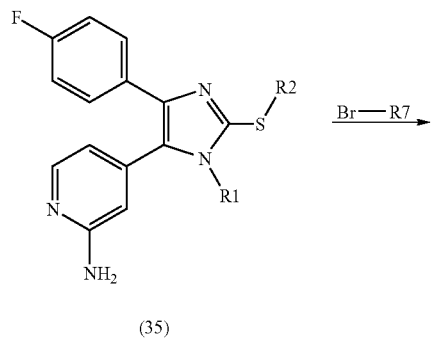

(35)

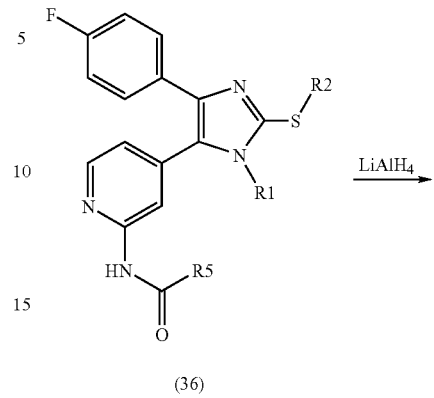

(36)

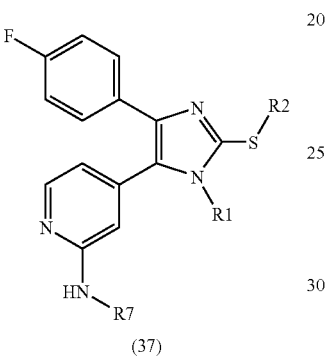

(37)

(39)

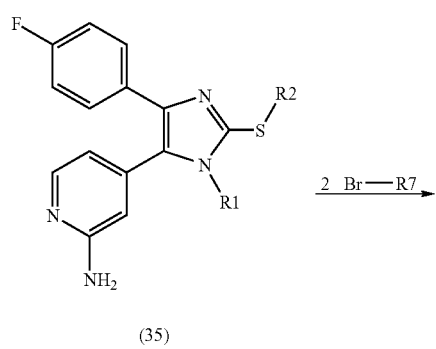

(35)

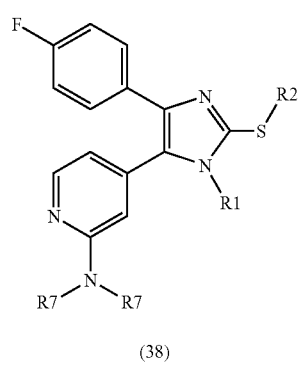

(38)

The amino group of the starting material 2-amino-γ-picolin (24) is protected, for example by introduction of an acetyl group using acetic anhydride. The methyl group of the compound (25) is then oxidized to the carboxyl group using, for example, potassium permanganate in an aqueous medium at from 20 to 90° C.

The reaction of the resulting pyridinecarboxylic acid (26) with 4-fluorophenyl-acetonitrile to give compound (27) and the subsequent removal of the nitrile group are carried out in accordance with variant 1. This also results in the removal of the acetyl group on the amino group of the pyridine compound, with the compound (28) being formed.

In the next step, the amino group is again protected, for example by introducing an acetyl group using acetic anhydride. The resulting compound (29) is, in accordance with variant 1 or 2 (shown in scheme 8 using variant 1), converted into the thiono compound (32). Into this compound, the desired radical $R^2$ is introduced as described in schemes 3, 4 and 7.

To introduce the desired substituent into the pyridyl group, the acetyl group is initially removed hydrolytically, for example using aqueous acid, giving the amino compound (35). An acyl radical is introduced by acylation, in particular with the corresponding acid chloride $R^5COCl$ in an inert solvent, such as an ether, for example tetrahydrofuran or dioxane, or in a chlorinated hydrocarbon, for example methylene chloride or 1,2-dichloroethan, etc. The acylation is generally carried out in the presence of a base, for example triethylamine, in an at least equimolar amount.

To prepare the substituted amine compounds, compound (35) is reacted with one or two molar equivalents of an alkyl bromide or phenylalkyl bromide in an inert solvent, such as dimethylformamide, in the presence of a base, such as sodium hydride, to give the compounds (37) or (38). Alternatively, the amide compounds (34) or (36) can be reduced with lithium aluminum hydride, for example in tetrahydrofuran, to give compound 39.

In vitro and in vivo, the compounds according to the invention show immunomodulating and cytokine-release inhibiting action. Cytokines are proteins such as TNF-α and IL-β which play an important role in numerous inflammatory disorders. The compounds according to the invention are, owing to their cytokine-release-inhibiting action, suitable for treating disorders which are associated with a disturbance of the immune system. They are suitable, for example, for treating autoimmune disorders, cancer, rheumatoid arthritis, gout, septic shock, osteoporosis, neuropathic pain, the spread of HIV, HIV dementia, viral myocarditis, insulin-dependent diabetes, periodontal disorders, restenosis, alopecia, T-cell depletion associated with HIV infections or AIDS, psoriasis, acute pancreatitis, rejection reactions of allogenic transplants, allergic pneumonia, arteriosclerosis, multiple sclerosis, cachexia, Alzheimer's disease, stroke, ictus, colitis ulcerosa, morbus Crohn, inflammatory bowel disease (IBD), ischemia, congestive heart failure, pulmonary fibrosis, hepatitis, glioblastoma, Guillain-Barre syndrome, systemic lupus erythematodes, adult respiratory distress syndrome (ARDS) and respiratory distress syndrome.

The compounds according to the invention can be administered either as individual therapeutically active compounds or as mixtures with other therapeutically active compounds. The compounds can be administered on their own; in general, however, they are formulated and administered in the form of pharmaceutical compositions, i.e. as mixtures of the active compounds with suitable pharmaceutical carriers or diluents. The compounds or compositions can be administered orally or parenterally; preferably, they are administered in oral dosage forms.

The type of pharmaceutical composition or carrier or diluent depends on the desired administration form. Oral compositions, for example, can be present as tablets or capsules and may comprise customary excipients, such as binders (for example syrup, gum arabic, gelatin, sorbitol, tragacanth or polyvinylpyrrolidone), fillers (for example lactose, sugar, cornstarch, calcium phosphate, sorbitol or glycerol), glidants (for example magnesium stearate, talc, polyethylene glycol or silica), disintegrants (for example starch) or wetting agents (for example sodium lauryl sulfate). Liquid oral preparations can assume the form of aqueous or oily suspensions, solutions, emulsions, syrups, elixirs or sprays and the like. They can also be present as a dry powder which is reconstituted using water or another suitable carrier. Such liquid preparations may comprise customary additives, for example suspending agents, flavors, diluents or emulsifiers. For parenteral administration, it is possible to use solutions or suspensions with customary pharmaceutical carriers.

The compounds or compositions according to the invention can be administered to mammals (man or animal) in a dose of from about 0.5 mg to 100 mg per kg of body weight per day. They may be administered in one individual dose or in a plurality of doses. The activity spectrum of the compounds as inhibitors of cytokine release was examined using the test systems below, as described by C. Donat and S. Laufer in Arch. Pharm. Pharm. Med. Chem. 333, Suppl. 1, 1-40, 2000.

In vitro Test with Human Whole Blood

The test substance is added to samples of human potassium-EDTA whole blood (of 400 μl each) and the samples are preincubated in a $CO_2$ incubator (5% $CO_2$; 95% moisture-saturated air) at 37° C. for 15 min. The samples are then stimulated with 1 μg/ml of LPS (*E.coli* 026:B6) at 37° C. in a $CO_2$ incubator (5% $CO_2$; 95% moisture-saturated air) for 4 hours. The reaction is stopped by placing the samples on ice, adding DPBS buffer and then centrifuging at 1000*g for 15 min. The amount of IL-1β and TNFα in the plasma supernatant is then determined by ELISA.

In vitro Test with PBMCs

The mononuclear cells (PBMCs) from human potassium-EDTA whole blood, diluted 1:3, are isolated by density gradient centrifugation (Histopaque®-1.077). The cells are washed twice with DPBS buffer, resuspended in macrophage SFM medium and adjusted to a cell count of $1*10^6$ cells/ml.

The resulting PBMCs suspension (samples of in each case 390 μl) and the test substance are preincubated at 37° C. in a $CO_2$ incubator (5% $CO_2$; 95% moisture-saturated air) for 15 min. The samples are then stimulated with in each case 1 μl/ml of LPS (*E.coli* 026:B6) at 37° C. in a $CO_2$ incubator (5% $CO_2$; 95% moisture-saturated air) for 4 hours. The reaction is stopped by placing the samples on ice, adding DPBS buffer and then centrifuging at 15 880*g for 12 min. The amount of IL-1β and TNFα in the plasma supernatant is then determined by ELISA.

The results of the in vitro tests are shown in tables 1 and 2 below.

TABLE 1

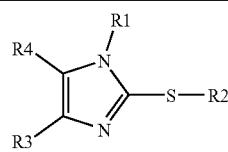

| Example | R1 | R2 | R3 | R4 | Yield[b] | TNF-α[a] | IL-1β[a] |
|---|---|---|---|---|---|---|---|
| 1 | $CH_3$ | H | 4-F-phenyl | 4-pyridyl | 36 | 19 | 3.6 |
| 2 | $C_2H_5$ | H | 4-F-phenyl | 4-pyridyl | 11 | 41 | 1.3 |
| 3 | $n-C_3H_7$ | H | 4-F-phenyl | 4-pyridyl | 31/22 | 32 | 2.4 |
| 4 | $i-C_3H_7$ | H | 4-F-phenyl | 4-pyridyl | 15 | 46% | 2.2 |

TABLE 1-continued

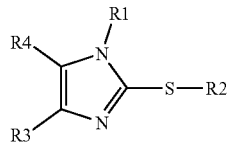

| Example | R1 | R2 | R3 | R4 | Yield[b] | TNF-α[a] | IL-1β[a] |
|---|---|---|---|---|---|---|---|
| 5 | cyclohexyl | H | 4-F-phenyl | 4-pyridyl | 9 | 33 | 5.4 |
| 6 | cyclopropyl | H | 4-F-phenyl | 4-pyridyl | 33 | —[b] | — |
| 7 | phenyl | H | 4-F-phenyl | 4-pyridyl | 7 | 37 | 2.3 |
| 8 | benzyl | H | 4-F-phenyl | 4-pyridyl | 8 | 20 | 1.0 |
| 9 | 4-dimethylaminophenyl | H | 4-F-phenyl | 4-pyridyl | 8 | 15 | 1.8 |
| 10 | 3-pyridyl | H | 4-F-phenyl | 4-pyridyl | 16 | 42% | 8.0 |
| 11 | dimethylaminoethyl | H | 4-F-phenyl | 4-pyridyl | 15 | 19% | 12 |
| 12 | 2,2,6,6-tetramethylpiperidin-4-yl | H | 4-F-phenyl | 4-pyridyl | 13 | 45 | 1.6 |
| 13 | dimethylaminopropyl | H | 4-F-phenyl | 4-pyridyl | 22 | — | — |
| 14 | N-morpholinopropyl | H | 4-F-phenyl | 4-pyridyl | 38 | 100 | 18 |
| 15 | 4-methylsulfanylphenyl | H | 4-F-phenyl | 4-pyridyl | 13 | — | — |
| 16 | N-morpholinoethyl | H | 4-F-phenyl | 4-pyridyl | 16 | 34% | 44% |
| 17 | 3-hydroxypropyl | H | 4-F-phenyl | 4-pyridyl | 13 | 49% | 7.3 |
| 18 | 1-benzylpiperidin-4-yl | H | 4-F-phenyl | 4-pyridyl | 18 | 38 | 5.8 |
| 19 | allyl | H | 4-F-phenyl | 4-pyridyl | 28 | — | — |
| 20 | $CH_3$ | $CH_3$ | 4-F-phenyl | 4-pyridyl | 15 | 2.5 | 0.45 |
| 21 | $n\text{-}C_3H_7$ | $CH_3$ | 4-F-phenyl | 4-pyridyl | 6 | 1.3 | 0.36 |
| 22 | cyclopropyl | $CH_3$ | 4-F-phenyl | 4-pyridyl | 12 | 1.1 | 0.34 |
| 23 | N-morpholinoethyl | $CH_3$ | 4-F-phenyl | 4-pyridyl | 3 | | |
| 24 | N-morpholinopropyl | $CH_3$ | 4-F-phenyl | 4-pyridyl | 4 | 2.7 | 1.0 |
| 25 | 2,2,6,6-tetramethylpiperidin-4-yl | $CH_3$ | 4-F-phenyl | 4-pyridyl | 11 | 16 | 0.85 |
| 26 | 1-benzylpiperidin-4-yl | $CH_3$ | 4-F-phenyl | 4-pyridyl | 3 | — | — |
| 27 | $C_2H_5$ | $4\text{-}CH_3\text{---}SO_2\text{-benzyl}$ | 4-F-phenyl | 4-pyridyl | 6 | 4.1 | 0.95 |
| 28 | $n\text{-}C_3H_7$ | benzyl | 4-F-phenyl | 4-pyridyl | 24 | 29 | 0.65 |
| 29 | $n\text{-}C_3H_7$ | 4-Cl-benzyl | 4-F-phenyl | 4-pyridyl | 20 | 62 | 1.3 |
| 30 | $n\text{-}C_3H_7$ | $4\text{-}CH_3\text{-benzyl}$ | 4-F-phenyl | 4-pyridyl | 20 | 22 | 1.3 |
| 31 | $n\text{-}C_3H_7$ | $4\text{-}CH_3\text{---}S\text{-benzyl}$ | 4-F-phenyl | 4-pyridyl | 12 | 35% | 4.7 |
| 32 | $n\text{-}C_3H_7$ | $4\text{-}CH_3\text{---}SO\text{-benzyl}$ | 4-F-phenyl | 4-pyridyl | 3 | 24 | 1.6 |
| 33 | $n\text{-}C_3H_7$ | $4\text{-}CH_3\text{---}SO_2\text{-benzyl}$ | 4-F-phenyl | 4-pyridyl | 9 | 6.8 | 0.72 |
| 34 | $i\text{-}C_3H_7$ | 4-Cl-benzyl | 4-F-phenyl | 4-pyridyl | 6 | 53 | 5.3 |
| 35 | $i\text{-}C_3H_7$ | $4\text{-}CH_3\text{---}SO_2\text{-benzyl}$ | 4-F-phenyl | 4-pyridyl | 7 | 2.7 | 1.5 |
| 36 | cyclopropyl | $\text{---}CH_2\text{---}CH\text{=}CH\text{-phenyl}$ | 4-F-phenyl | 4-pyridyl | 27 | — | — |
| 37 | cyclopropyl | $\text{---}CH_2\text{---}CH\text{=}CH\text{-}4\text{-}Cl\text{-phenyl (trans)}$ | 4-F-phenyl | 4-pyridyl | 11 | — | — |
| 38 | cyclopropyl | $\text{---}CH_2\text{---}CH\text{=}CH\text{-phenyl}$ | 4-F-phenyl | 4-pyridyl | 12 | — | — |
| 39 | cyclohexyl | $4\text{-}CH_3\text{---}SO_2\text{-benzyl}$ | 4-F-phenyl | 4-pyridyl | 5 | 13 | 1.8 |
| 40 | phenyl | $4\text{-}CH_3\text{---}SO_2\text{-benzyl}$ | 4-F-phenyl | 4-pyridyl | 2 | 3.4 | 1.3 |
| 41 | benzyl | $4\text{-}CH_3\text{---}SO_2\text{-benzyl}$ | 4-F-phenyl | 4-pyridyl | 3 | 1.0 | 0.36 |
| 42 | N-morpholinoethyl | benzyl | 4-F-phenyl | 4-pyridyl | 5 | 11 | 1.3 |
| 43 | N-morpholinopropyl | benzyl | 4-F-phenyl | 4-pyridyl | 25 | 5.4 | 0.89 |
| 44 | N-morpholinopropyl | $4\text{-}CH_3\text{---}SO_2\text{-benzyl}$ | 4-F-phenyl | 4-pyridyl | 31 | 12 | 1.4 |
| 45 | N-morpholinopropyl | $4\text{-}CH_3\text{---}SO\text{-benzyl}$ | 4-F-phenyl | 4-pyridyl | 4 | 12 | 2.4 |
| 46 | 2,2,6,6-tetramethylpiperidin-4-yl | benzyl | 4-F-phenyl | 4-pyridyl | 9 | 12 | 0.87 |
| 47 | $CH_3$ | N-morpholinoethyl | 4-F-phenyl | 4-pyridyl | 26 | 28 | 1.7 |
| 48 | $CH_3$ | cis-phenylethenyl | 4-F-phenyl | 4-pyridyl | 10 | 22 | 1.7 |
| 49 | $n\text{-}C_3H_7$ | cis-phenylethenyl | 4-F-phenyl | 4-pyridyl | 20 | — | — |
| 50 | cyclopropyl | cis-phenylethenyl | 4-F-phenyl | 4-pyridyl | 3 | — | — |
| 51 | $n\text{-}C_3H_7$ | $\text{---}CHBr\text{---}CHBr\text{-phenyl}$ | 4-F-phenyl | 4-pyridyl | 20 | — | — |
| 52 | $n\text{-}C_3H_7$ | phenyl | 4-F-phenyl | 4-pyridyl | 26 | 14 | 1.0 |
| 53 | $n\text{-}C_3H_7$ | 4-Cl-phenyl | 4-F-phenyl | 4-pyridyl | 25 | 29 | 3.3 |
| 54 | $n\text{-}C_3H_7$ | $4\text{-}CH_3\text{---}S\text{-phenyl}$ | 4-F-phenyl | 4-pyridyl | 22 | 68 | 2.5 |
| 55 | $n\text{-}C_3H_7$ | $4\text{-}CH_3\text{---}SO\text{-phenyl}$ | 4-F-phenyl | 4-pyridyl | 16 | 6.2 | 0.72 |
| 56 | $n\text{-}C_3H_7$ | $4\text{-}CH_3\text{---}SO_2\text{-phenyl}$ | 4-F-phenyl | 4-pyridyl | 15 | 19 | 1.5 |
| 57 | 4-F-phenyl | H | $CH_3$ | 4-pyridyl | 7 | 34% | 19 |
| 58 | 3-pyridyl | H | 4-F-phenyl | $CH_3$ | 15 | 32% | 28 |
| 59 | $n\text{-}C_3H_7$ | H | 4-pyridyl | 4-F-phenyl | 5 | 83 | 16% |
| 60 | N-morpholinoethyl | H | 4-pyridyl | 4-F-phenyl | 5 | — | — |

[a] $IC_{50}[\mu mol \times l^{-1}]$
[b] Total yield [%] for all steps

TABLE 2

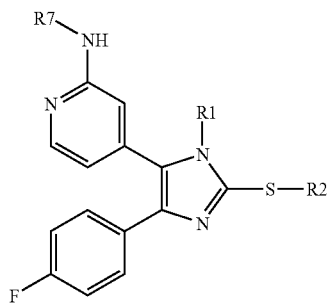

| Ex. | R1 | R7 | R2 | TNF-α[a)] | IL-1β[a)] |
|---|---|---|---|---|---|
| 61 | CH₃ | —COCH₃ | CH₃ | 0.87 | 0.07 |
| 62 | C₃H₇ | —COCH₃ | CH₃ | 0.49 | 0.12 |
| 63 | 2,2,6,6-tetramethylpiperidin-4-yl | —COCH₃ | CH₃ | 4.5 | 0.46 |
| 64 | N-morpholinopropyl | —COCH₃ | CH₃ | — | — |
| 65 | 3-hydroxypropyl | —COCH₃ | CH₃ | — | — |
| 66 | CH₃ | —H | CH₃ | 2.3 | 0.27 |
| 67 | CH₃ | -p-methoxybenzoyl | CH₃ | 0.64 | 0.44 |
| 68 | CH₃ | —CO-cyclopropyl | CH₃ | — | — |
| 69 | CH₃ | —CO-cyclopentyl | CH₃ | — | — |
| 70 | CH₃ | —Bz | CH₃ | 0.39 | 0.08 |
| 71 | CH₃ | -1-phenylethyl | CH₃ | 0.13 | 0.01 |
| 73 | CH₃ | —C₂H₅ | CH₃ | 0.35 | 0.05 |
| 74 | C₃H₇ | —C₂H₅ | CH₃ | 0.41 | 0.15 |
| 75 | 2,2,6,6-tetramethylpiperidin-4-yl | —C₂H₅ | CH₃ | 2.9 | 0.62 |
| 76 | N-morpholinopropyl | —COCH₃ | 4-methylsulfinylbenzyl | — | — |

[c)]$IC_{50}[\mu mol \times l^{-1}]$
Bz = benzyl

The compounds according to the invention and the processes for their preparation are now described in more detail using the examples below, without limiting the invention.

EXAMPLES

Example 1

4-(4-fluorophenyl)-1-methyl-5-(4-pyridyl)-2-thioimidazole a) 2-Cyano-2-(4-fluorophenyl)-1-(4-pyridyl)ethane 250 ml of dry ethanol were added dropwise to metallic sodium (17.3 g/0.7 mol). Ethyl isonicotinate (75.8 g/0.5 mol) and 4-fluorophenylacetonitrile (67.6 g/0.5 mol) were then added dropwise, and the mixture was subsequently heated under reflux for 15 min. After cooling, 600 ml of distilled water were added to the mixture. When the mixture was acidified to pH 1 using concentrated hydrochloric acid (HCl), the desired compound 2-cyano-2-(4-fluorophenyl)-1-(4-pyridyl)ethane precipitated as a yellow precipitate. The precipitate was filtered off, washed with distilled water and dried under reduced pressure over phosphorus pentoxide (P₂O₅). The yield was 85.0 g (62%).

b) 2-(4-Fluorophenyl)-1-(4-pyridyl)ethanone

2-Cyano-2-(4-fluorophenyl)-1-(4-pyridyl)ethane (40.6 g/0.15 mol) from example 1a was suspended in 300 ml of 48% strength hydrobromic acid (HBr), and the reaction mixture was heated under reflux for 18 h. After cooling, the mixture was adjusted to pH 9 using aqueous ammonia. The compound mentioned in the title, which precipitated during this operation, was filtered off, washed with distilled water and dried under reduced pressure over P₂O₅. The yield was 25.6 g (80%).

c) 2-(4-Fluorophenyl)-1-(4-pyridyl)-α-hydroxyiminoethanone 15.0 g (0.07 mol) of 2-(4-fluorophenyl)-1-(4-pyridyl) ethanone from example 1b were dissolved in 70 ml of glacial acetic acid. A solution of 4.8 g (0.07 mol) of NaNO₂ in 11 ml of water was slowly added dropwise to the initial charge, and the reaction mixture was stirred at room temperature. After 3 h, 400 ml of distilled water were added, and the mixture was stirred at room temperature for another 3 h. The compound (3) mentioned in the title precipitated out. The compound was filtered off, washed with distilled water and dried under reduced pressure over P₂O₅. The yield was 15.2 g (90%).

d) 4-(4-Fluorophenyl)-1-methyl-5-(4-pyridyl)imidazole N-oxide 2.0 g of 2-(4-fluorophenyl)-1-(4-pyridyl)-α-hydroxyiminoethanone from example 1c above and twice the equivalent amount of 1,3,5-trimethylhexahydro-1,3,5-triazine were dissolved in 20 ml of dry ethanol and heated under reflux for 10 h. After cooling, the ethanol was removed using a rotary evaporator. The slightly oily residue solidified on addition of diethyl ether. The precipitate was filtered off and dried under reduced pressure. The yield was 82%.

e) 4-(4-Fluorophenyl)-1-methyl-5-(4-pyridyl)imidazole-2-thione 0.5 g of 5-(4-fluorophenyl)-4-(4-pyridyl)-3-methylimidazole N-oxide from example 1d were dissolved in 20 ml of CHCl₃, and the reaction mixture was cooled in an ice-bath. An equimolar solution of 2,2,4,4-tetramethyl-3-thionocyclobutanone in CHCl₃ was slowly added dropwise to the initial charge, and the mixture was then stirred in the ice-bath for 30 min. The ice-bath was removed, and stirring was continued at room temperature for 1 h. The solvent was then removed using a rotary evaporator, and the solid residue was triturated in diethyl ether. The precipitate was filtered off and dried under reduced pressure. The yield was 98%.

IR: $1/\lambda$ (cm$^{-1}$)=1601, 1506, 1229, 1004, 843, 832

$^1$H NMR (d$_6$-DMSO, ppm): 12.95 (bs, 1H), 8.69-8.66 (m, 2H), 7.45-7.42 (m, 2H), 7.27-7.12 (m, 4H), 3.39 (s, 3H)

Example 2

1-Ethyl-4-(4-fluorophenyl)-5-(4-pyridyl)-2-thioimidazole a) 1-Ethyl-4-(4-fluorophenyl)-5-(4-pyridyl)imidazol-2-one Initially, 2-(4-fluorophenyl)-1-(4-pyridyl)-α-hydroxyiminoethanone was prepared as described in example 1, steps (a) to (c). 4.0 g of the iminoethanone were then, together with the equimolar amount of ethylamine and the equimolar amount of formaldehyde (36% strength aqueous solution), heated under reflux for 4 h. After cooling, the reaction mixture was neutralized using aqueous ammonia and extracted three times with CH$_2$Cl$_2$. The organic phases were combined and dried over Na$_2$SO$_4$. The drying agent was filtered off and the solvent was removed using a rotary evaporator. The slightly oily residue was solidified by addition of diethyl ether. The precipitate was filtered off and dried under reduced pressure. The yield was 63%.

b) 2-Chloro-1-ethyl-4-(4-fluorophenyl)-5-(4-pyridyl)imidazole 35 ml of POCl$_3$ and a small amount of NH$_4$Cl were added to 2.0 g of 1-ethyl-4-(4-fluorophenyl)-5-(4-pyridyl)imidazol-2-one, and the reaction mixture was heated under reflux for 9 h. After cooling, most of the excess POCl$_3$ was distilled off, and distilled water was carefully added to the residue. The mixture was neutralized using 20% strength NaOH, resulting in the precipitation of the title compound. The precipitate was filtered off and dried over P$_2$O$_5$ under reduced pressure. Yield: 81%.

c) 1-Ethyl-4-(4-fluorophenyl)-5-(4-pyridyl)imidazole-2-thione

NaH (4.5 eq.) was suspended in 10 ml of DMF, and 4-chlorobenzylthiol (4.5 eq.) was slowly added dropwise. The reaction mixture was stirred at room temperature for 45 min. 2.0 g of the 2-chloro-1-ethyl-4-(4-fluorophenyl)-5-(4-pyridyl)imidazole obtained in the step above were then added. The mixture was heated under reflux for 10 h. After cooling, distilled water was added to the mixture, the pH was adjusted to 1 using concentrated HCl and the mixture was washed six times with diethyl ether. Neutralization of the aqueous phase with 20% strength NaOH resulted in the precipitation of the title compound. The precipitate was filtered off and dried over P$_2$O$_5$ under reduced pressure. Purification was by recrystallization. The yield was 50%.

IR: $1/\lambda$ (cm$^{-1}$)=3059, 1587, 1498, 1220, 837, 814

$^1$H NMR (CDCl$_3$, ppm): 12.63 (bs, 1H), 8.74-8.72 (m, 2H), 7.27-7.17 (m, 4H), 7.0-6.90 (m, 2H), 4.08 (q, 2H, J=7.1 Hz), 1.21 (t, 3H, J=7.1 Hz)

Example 3A 4-(4-Fluorophenyl)-1-n-propyl-5-(4-pyridyl)-2-thioimidazole

The process of example 1 was employed, where step d) the 2-(4-fluorophenyl)-1-(4-pyridyl)-α-hydroxyiminoethanone was reacted with twice the equivalent amount of 1,3,5-tri-n-propylhexahydro-1,3,5-triazine.

The yield was in the range of 60-91%.

IR: $1/\lambda$ (cm$^{-1}$)=2932, 1586, 1500, 1221, 831, 814

$^1$H NMR (CDCl$_3$, ppm): 12.47 (bs, 1H), 8.76-8.73 (m, 2H), 7.26-7.13 (m, 4H), 7.0-6.96 (m, 2H), 3.98 (t, 2H, J=7.8 Hz), 1.65 (m, 2H), 0.82 (t, 3H, J=7.4 Hz)

Example 3B 4-(4-Fluorophenyl)-1-n-propyl-5-(4-pyridyl)-2-thioimidazole

Alternatively, to prepare the title compound, the process of example 2 was employed, where step a) 2-(4-fluorophenyl)-1-(4-pyridyl)-α-hydroxyiminoethanone was reacted with the equimolar amount of n-propylamine.

The yield was in the range of 32-72%.

Example 4

4-(4-Fluorophenyl)-1-isopropyl-5-(4-pyridyl-2-thioimidazole

To prepare the title compound, the process of example 2 was employed, where in step a) 2-(4-fluorophenyl)-1-(4-pyridyl)-α-hydroxyiminoethanone was reacted with the equimolar amount of isopropylamine.

IR: $1/\lambda$ (cm$^{-1}$)=3040, 1584, 1500, 1230, 841, 819

$^1$H NMR (CDCl$_3$, ppm): 11.73 (bs, 1H), 8.76-8.74 (m, 2H,), 7.28 (m, 2H), 7.17-7.10 (m, 2H), 7.0-6.92 (m, 2H), 4.89 (m, 1H), 1.48 (s, 3H), 1.45 (s, 3H)

Example 5

1-Cyclohexyl-4-(4-fluorophenyl)-5-(4-pyridyl)-2-thioimidazole

To prepare the title compound, the process of example 2 was used, where in step a) 2-(4-fluorophenyl)-1-(4-pyridyl)-α-hydroxyiminoethanone was reacted with the equimolar amount of cyclohexylamine.

IR: $1/\lambda$ (cm$^{-1}$)=2934, 1560, 1505, 1228, 842

$^1$H NMR (CDCl$_3$, ppm): 11.32 (bs, 1H), 8.76-8.73 (m, 2H), 7.30-7.31 (m, 2H), 7.15-7.08 (m, 2H), 7.01-6.92 (m, 2H), 4.60-4.25 (m, 1H), 2.0-1.18 (m, 10H)

Example 6

1-Cyclopropyl-4-(4-fluorophenyl)-5-(4-pyridyl)-2-thioimidazole

The same process as in example 1 was used, where in step d) the 2-(4-fluorophenyl)-1-(4-pyridyl)-α-hydroxyiminoethanone was reacted with twice the equivalent amount of 1,3,5-tricyclopropylhexahydro-1,3,5-triazine.

IR: $1/\lambda$ (cm$^{-1}$)=3013, 1589, 1515, 1499, 1487, 1223, 830, 685

1H NMR (CDCl$_3$, ppm): 12.76 (bs, 1H), 8.68-8.65 (m, 2H), 7.26-7.19 (m, 4H), 7.07-6.99 (m, 2H), 3.12-3.08 (m, 1H), 1.02-0.95 (m, 2H), 0.76-0.71 (m, 2H)

Example 7

4-(4-Fluorophenyl)-1-phenyl-5-(4-pyridyl)-2-thio-imidazole

To prepare the title compound, the process of example 2 was employed, where in step a) 2-(4-fluorophenyl)-1-(4-pyridyl)-α-hydroxyiminoethanone was reacted with the equimolar amount of aniline.

IR: $1/\lambda$ (cm$^{-1}$)=2880, 1597, 1504, 1227, 844, 825
$^1$H NMR (CDCl$_3$, ppm): 11.58 (bs, 1H), 8.48-8.41 (m, 2H), 7.78-6.74 (m, 11H)

Example 8

1-Benzyl-4-(4-fluorophenyl)-5-(4-pyridyl)-2-thio-imidazole

To prepare the title compound, the process of example 2 was employed, where in step a) 2-(4-fluorophenyl)-1-(4-pyridyl)-α-hydroxyiminoethanone was reacted with the equimolar amount of benzylamine.

IR: $1/\lambda$ (cm$^{-1}$)=3032, 1587, 1497, 1225, 1158, 837, 816
$^1$H NMR (CDCl3, ppm): 12.88 (bs, 1H), 8.56-8.53 (m, 2H), 7.27-6.90 (m, 11H), 5.28 (s, 2H)

Example 9

1-Dimethylaminophenyl-4-(4-fluorophenyl)-5-(4-pyridyl)-2-thioimidazole

To prepare the title compound, the process of example 2 was employed, where in step a) 2-(4-fluorophenyl)-1-(4-pyridyl)-α-hydroxyiminoethanone was reacted with the equimolar amount of 4-dimethylaminobenzylamine.

IR: $1/\lambda$ (cm$^{-1}$)=2891, 1606, 1500, 1357, 1225, 835, 816
$^1$H NMR (d$_6$-DMSO, ppm): 13.05 (bs, 1H), 8.43-8.41 (m, 2H), 7.37-7.03 (m, 8H), 6.98-6.60 (m, 2H), 2.89 (s, 6H)

Example 10

4-(4-Fluorophenyl)-1-(3-pyridyl)-5-(4-pyridyl)-2-thioimidazole

To prepare the title compound, the process of example 2 was employed, where in step a) 2-(4-fluorophenyl)-1-(4-pyridyl)-α-hydroxyiminoethanone was reacted with the equimolar amount of 3-pyridylamin.

IR: $1/\lambda$ (cm$^{-1}$)=3035, 1597, 1478, 1433, 1433, 1224, 813, 708
$^1$H NMR (d$_6$-DMSO, ppm): 13.34 (s, 1H), 8.54-8.45 (m, 4H), 7.76-7.75 (m, 1H), 7.40-7.13 (m, 7H)

Example 11

1-Dimethylaminoethyl-4-(4-fluorophenyl)-5-(4-pyridyl)-2-thioimidazole

The same process as in example 1 was used, where in step d) the 2-(4-fluoro-phenyl)-1-(4-pyridyl)-α-hydroxyiminoethanone was reacted with twice the equivalent amount of 1,3,5-tri(2-dimethylaminoethyl)hexahydro-1,3,5-triazine.

IR: $1/\lambda$ (cm$^{-1}$)=2772, 1597, 1503, 1225, 835, 815
$^1$H NMR (CDCl$_3$, ppm): 8.74-8.72 (m, 2H), 7.30-7.17 (m, 4H), 7.04-6.94 (m, 2H), 4.13 (t, 2H, J=6.8 Hz), 2.56 (t, 2H, J=6.7 Hz), 2.11 (s, 6H)

Example 12

4-(4-Fluorophenyl)-5-(4-pyridyl)-1-(2,2,6,6-tetramethylpiperidin-4-yl)-2-thioimidazole The same process as in example 1 as employed, where in step d) the 2-(4-fluorophenyl)-1-(4-pyridyl)-α-hydroxyiminoethanone was reacted with twice the molar amount of 2,2,6,6-tetramethyl-4-methyleneaminopiperidine.

IR: $1/\lambda$ (cm$^{-1}$)=2964, 1587, 1498, 1352, 1234, 838, 815

Example 13

1-Dimethylaminopronyl-4-(4-fluorophenyl)-5-(4-pyridyl)-2-thioimidazole

The same process as in example 1 was employed, where in step d) the 2-(4-fluorophenyl)-1-(4-pyridyl)-α-hydroxyiminoethanone was [lacuna] with twice the equivalent amount of 1,3,5-tri(3-dimethylaminopropyl)hexahydro-1,3,5-triazine.

Example 14

4-(4-Fluorophenyl)-1-(3-N-morpholinopropyl)-5-(4-pyridyl)-2-thioimidazole

The same process as in example 1 was employed, where in step d) the 2-(4-fluorophenyl)-1-(4-pyridyl)-α-hydroxyiminoethanone was reacted with twice the equivalent amount of 1,3,5-tri(N-morpholinopropyl)hexahydro-1,3,5-triazine.

IR: $1/\lambda$ (cm$^{-1}$)=2847, 1502, 1233, 1114, 842, 817
$^1$H NMR (CDCl$_3$, ppm): 12.11 (bs, 1H), 8.75-8.71 (m, 2H), 7.26-7.18 (m, 4H), 7.05-6.95 (m, 2H), 4.15-4.07 (m, 2H), 3.61-3.57 (m, 4H), 2.32-2.23 (m, 6H), 1.86-1.75 (m, 2H)

Example 15

4-(4-Fluorophenyl)-1-(4-methylsulfanylphenyl)-5-(4-pyridyl)-2-thio-imidazole The same process as in example 1 was employed, where in step d) the 2-(4-fluorophenyl)-1-(4-pyridyl)-α-hydroxyiminoethanone was reacted with twice the equivalent amount of 1,3,5-tri(4-methylsulfanylphenyl)hexahydro-1,3,5-triazine.

IR: $1/\lambda$ (cm$^{-1}$)=2693, 1597, 1495, 1220, 844, 817
$^1$H NMR (CDCl$_3$, ppm): 12.43 (bs, 1H), 8.47-8.44 (m, 2H), 7.32-7.12 (m, 6H), 7.06-6.97 (m, 2H), 6.90-6.87 (m, 2H), 2.50 (s, 3H)

Example 16

4-(4-Fluorophenyl)-1-N-morpholinoethyl-5-(4-pyridyl)-2-thioimidazole

The same process as in example 1 was employed, where in step d) the 2-(4-fluorophenyl)-1-(4-pyridyl)-α-hydroxyiminoethanone was reacted with twice the equivalent amount of 1,3,5-tri(N-morpholinoethylhexahydro-1,3,5-triazine.

IR: $1/\lambda$ (cm$^{-1}$)=2813, 1599, 1508, 1232, 1117, 850, 835
$^1$H NMR (d$_6$-DMSO): 12.91 (bs, 1H), 8.71-8.68 (m, 2H), 7.49-7.46 (m, 2H), 7.25-7.16 (m, 4H), 4.04 (t, 2H, J=Hz), 2.40 (t, 2H, J=Hz), 2.16 (t, 4H, J=3.8 Hz)

Example 17

4-(4-Fluorophenyl)-1-(3-hydroxypronyl)-5-(4-pyridyl)-2-thioimidazole

The same process as in example 1 was employed, wherein in step d) the 2-(4-fluorophenyl)-1-(4-pyridyl)-α-hydroxyiminoethanone was reacted with twice the equivalent amount of 1,3,5-tri(3-hydroxypropylhexahydro-1,3,5-triazine.

IR: $1/\lambda$ (cm$^{-1}$)=3049, 2926, 1499, 1223, 1162, 1061, 838
$^1$H NMR (d$_6$-DMSO, ppm): 12.98 (s, 1H), 8.71-8.68 (m, 2H), 7.47-7.44 (m, 2H), 7.29-7.12(m, 4H), 4.47-4.43 (bs, 1H), 3.97 (t, 2H, J=7.4 Hz), 3.27 (t, 2H, J=6.2 Hz), 1.68-1.54 (m, 2H)

Example 18

1-(1-Benzylpiperidin-4-yl-4-(4-fluorophenyl)-5-(4-pyridyl)-2-thioimidazole

The same process as in example 1 was employed, wherein in step d) the 2-(4-fluorophenyl)-1-(4-pyridyl)-α-hydroxyiminoethanone was reacted with twice the molar amount of 1-benzyl-4-methyleneaminopiperidine.

IR: $1/\lambda$ (cm$^{-1}$)=2903, 1504, 1247, 1227, 853, 741
$^1$H NMR (d$_6$-DMSO): 12.93 (s, 1H), 8.73-8.70 (m, 2H), 7.50-7.47 (m, 2H), 7.29-7.11 (m, 9H), 3.96-4.12 (m, 1H), 3.38 (s, 2H), 3.85-3.75 (m, 2H), 2.31-2.18 (m, 2H), 1.93-1.64 (m, 4H)

Example 19

1-Allyl-4-(4-fluorophenyl)-5-(4-pyridyl)-2-thioimidazole

The same process as in example 1 was employed, wherein in step d) the 2-(4-fluorophenyl)-1-(4-pyridyl)-α-hydroxyiminoethanone was reacted with twice the equivalent amount of 1,3,5-tri(prop-2-en-1-yl)hexahydro-1,3,5-triazine.

IR: $1/\lambda$ (cm$^{-1}$)=2695, 1700, 1600, 1506, 1421, 1227, 1005, 934, 927, 841, 829, 817
$^1$H NMR (CDCl$_3$, ppm): 12.49 (bs, 1H), 8.72-8.65 (m, 2H), 7.29-7.22 (m, 4H), 4H), 7.04-6.96 (m, 2H), 6.00-5.81 (m, 1H), 5.25-5.19 (m, 1H), 5.02-4.93 (m, 1H), 4.66-4.64 (m, 2H)

Example 20

4-(4-Fluorophenyl)-1-methyl-2-methylthio-5-(4-pyridylimidazole a) The 1-substituted 4-(4-fluorophenyl)-5-(4-pyridyl)imidazole-2-thione (compound 5 from scheme 1) was prepared as described in example 1, the added imine compound being 1,3,5-trimethylhexahydro-1,3,5-triazine.

b) To methylate the sulfur, 0.7 g of the resulting thione compound (5) was then suspended under protective gas in 20 ml of dry ethanol, and the equimolar amount of dimethyl sulfate or methyl iodide was added. A spatula tip of Na$_2$CO$_3$ was added, and the reaction mixture was then heated under reflux for 3 h. After cooling, the inorganic salts were filtered off and the solvent was removed using a rotary evaporator. The crude product was purified by column chromatography. The yield was 43%.

IR: $1/\lambda$ (cm$^{-1}$)=1603, 1510, 1220, 1160, 850, 830, 814

$^1$H NMR (CDCl$_3$, ppm): 8.70-8.67 (m, 2H), 7.43-7.36 (m, 2H), 7.24-7.22 (m, 2H), 6.98-6.89 (m, 2H), 3.47 (s, 3H), 2.72 (s, 3H)

Example 21

4-(4-Fluorophenyl)-2-methylthio-1-n-propyl-5-(4-pyridyl)imidazole

The title compound was prepared analogously to the process of example 20. 1,3,5-tri-n-propylhexahydro-1,3,5-triazine was used for cyclizing the imidazole compound.

IR: $1/\lambda$ (cm$^{-1}$)=2929, 1601, 1511, 1221, 849, 829, 816
$^1$H NMR (CDCl$_3$, ppm): 8.71-8.68 (m, 2H), 7.41-7.34 (m, 2H), 7.26-7.23 (m, 2H), 6.96-6.87 (m, 2H), 3.79 (t, 2H, J=7.7 Hz), 2.74 (s, 3H), 1.64-1.52 (m, 2H), 0.80 (t, 3H, J=7.4 Hz)

Example 22

1-Cyclopropyl-4-(4-fluorophenyl)-2-methylthio-5-(4-pyridyl)imidazole

The title compound was prepared analogously to the process of example 20. 1,3,5-tricyclopropylhexahydro-1,3,5-triazine was used for cyclizing the imidazole compound.

$^1$H NMR (CDCl$_3$, ppm): 8.64-8.61 (m, 2H), 7.41-7.34 (m, 2H), 7.27-7.24 (m, 2H, 6.98-6.90 (m, 2H), 3.13-3.02 (m, 1H), 2.74 (s, 3H), 0.95-0.91 (m, 2H), 0.70-0.66 (m, 2H)

Example 23

4-(4-Fluorophenyl)-2-methylthio-1-N-morpholinoethyl-5-(4-pyridyl)-imidazole

The title compound was prepared analogously to the process of example 20. 1,3,5-tri(N-morpholino)ethylhexahydro-1,3,5-triazinethanamine was used for cyclizing the imidazole compound.

IR: $1/\lambda$ (cm$^{-1}$)=2852, 1600, 1509, 1215, 1114, 871, 841, 813
$^1$H NMR (CDCl$_3$, ppm): 8.71-8.68 (m, 2H), 7.41-7.34 (m, 2H), 7.30 (m, 2H), 6.96-6.87 (m, 2H), 3.96 (t, 3H, J=7.0 Hz), 3.60 (t, 4H, J=4.6 Hz), 2.74 (s, 3H), 2.46 (t, 2H, J=7.0 Hz), 2.32 (t, 4H, J=4.7 Hz)

Example 24

4-(4-Fluorophenyl)-2-methylthio-1-N-morpholinopropyl-5-(4-pyridyl)-imidazole

The title compound was prepared analogously to the process of example 20. 1,3,5-tri(3-N-morpholinopropyl)hexahydro-1,3,5-triazine was used for cyclizing the imidazole compound.

IR: $1/\lambda$ (cm$^{-1}$)=2814, 1509, 1219, 1114, 842
$^1$H NMR (CDCl$_3$, ppm): 8.71-8.68 (m, 2H), 7.41-7.36 (m, 2H), 7.27-7.23 (m, 2H), 6.96-6.87 (m, 2H), 3.98-90 (m, 2H), 3.64-3.59 (m, 4H), 2.74 (s, 3H), 2.27-2.19 (m 6H), 1.77-1.68 (2H)

Example 25

4-(4-Fluorophenyl)-2-methylthio-5-(4-pyridyl)-1-(2,2,6,6-tetramethyl-piperidin-4-yl)imidazole The title compound was prepared analogously to the process of example 20. 2,2,6,6-tetramethyl-4-methylenaminopiperidine was used for cyclizing the imidazole compound.

IR: $1/\lambda$ (cm$^{-1}$)=2968, 1600, 1509, 1343, 1229, 1033, 835, 813

$^1$H NMR (CDCl$_3$, ppm): 8.73-8.70 (m, 2H), 7.37-7.22 (m, 4H), 6.94-6.86 (m, 2H), 4.41-4.28 (m, 1H), 2.75 (s, 3H), 2.05-2.04 (m, 2H), 1.74-1.66 (m, 2H), 1.16, 1.04 (2s, 12H)

Example 26

1-Benzylpiperidin-4-yl-4-(4-fluorophenyl)-2-methylthio-5-(4-pyridyl)-imidazole

The title compound was prepared analogously to the process of example 20. 1-benzyl-4-methylenaminopiperidine was used for cyclizing the imidazole compound.

IR: $1/\lambda$ (cm$^{-1}$)=2929, 2809, 1602, 1509, 1220, 1158, 840, 828, 814, 743, 701

$^1$H NMR (d$_6$-DMSO, ppm): 8.72-8.69 (m, 2H), 7.41-7.38 (m, 2H), 7.30-7.21 (m, 7H), 7.09-7.0 (m, 2H), 3.60-3.72 (m, 1H), 3.40 (s, 1H), 2.85-2.80 (m, 2H), 2.42-2.22 (m, 2H), 1.81-1.76 (m, 4H)

Example 27

1-Ethyl-4-(4-fluorophenyl)-2-(4-methylsulfonyl)benzylthio-5-(4-pyridyl)-imidazole a) The 1-substituted 4-(4-fluorophenyl)-5-(4-pyridyl)imidazole-2-thione (compound 5 of scheme 2) was prepared as described in example 2, the added amine compound being ethylamine.

b) To benzylate the sulfur, 0.4 g of the resulting thione compound (5) was suspended under protective gas in 15 ml of dry ethanol, and the equimolar amount of 4-methylsulfonylbenzyl chloride was added. A spatula tip of Na$_2$CO$_3$ was added, and the reaction mixture was then heated under reflux for 5 h. After cooling, the Na$_2$CO$_3$ was filtered off and the solvent was removed using a rotary evaporator. The crude product of the title compound (compound 9 in scheme 3.2) was purified by column chromatography.

Yield: 55%

IR: $1/\lambda$ (cm$^{-1}$)=1510, 1304, 1149, 841, 766

$^1$H NMR (CDCl$_3$, ppm): 8.71-8.69 (m, 2H), 7.91-7.87 (m, 2H), 7.62-7.58 (m, 2H), 7.41-7.34 (m, 2H), 7.26-7.21 (m, 2H), 6.98-6.91 (m, 2H), 4.52 (s, 2H), 3.73 (q, 2H, J=7.21 Hz), 3.05 (s, 3H), 1.07 (t, 3H, J=7.2 Hz)

Example 28

2-Benzylthio-4-(4-fluorophenyl)-1-n-propyl-5-(4-pyridyl)imidazole a) The 1-substituted 4-(4-fluorophenyl)-5-(4-pyridyl)imidazole-2-thione (compound 5 of scheme 1) was prepared as described in example 1, the added imine compound being 1,3,5-tri-n-propylhexahydro-1,3,5-triazine.

b) The sulfur was benzylated using benzyl chloride, following the process of example 27 (step b).

IR: $1/\lambda$ (cm$^{-1}$)=1602, 1510, 1220, 851, 833, 815, 695

$^1$H NMR (CDCl3, ppm): 8.70-8.67 (m, 2H), 7.43-7.26 (m, 6H), 7.19-7.16 (m, 2H), 6.98-6.89 (m, 2H), 4.39 (s, 2H), 3.56 (t, 2H, J=7.6 Hz), 1.42-1.30 (m, 2H), 0.66 (t, 3H, J=7.4 Hz)

Example 29

2-(4-Chlorobenzyl)thio-4-(4-fluorophenyl)-1-n-propyl-5-(4-pyridyl)-imidazole

The title compound was prepared as described in example 28, except that 4-chlorobenzyl chloride was used for the benzylation.

IR: $1/\lambda$ (cm$^{-1}$)=2972, 1602, 1509, 1343, 1222, 1092, 844, 828, 816, 743, 698

$^1$H NMR (CDCl$_3$, ppm): 8.71-8.68 (m, 2H), 7.41-7.34 (m, 2H), 7.27-7.26 (m, 4H), 7.19-7.16 (m, 2H), 6.98-6.89 (m, 2H), 4.38 (s, 2H), 3.61 (t, 2H, J=7.6 Hz), 1.45-1.33 (m, 2H), 0.68 (t, 3H, 7.4 Hz)

Example 30

4-(4-Fluorophenyl)-2-(4-methylbenzyl)thio-1-n-propyl-5-(4-pyridyl)-imidazole

The title compound was prepared as described in example 28, except that 4-methylbenzyl chloride was used for the benzylation.

IR: $1/\lambda$ (cm$^{-1}$)=2927, 1603, 1510, 1222, 849, 831, 815

$^1$H NMR (CDCl$_3$, ppm): 8.70-8.67 (m, 2H), 7.43-7.36 (m, 2H), 7.23-7.09 (m, 6H), 6.98-6.89 (m, 2H), 4.37 (s, 2H), 3.59 (t, 2H, J=7.7 Hz), 2.34 (s, 3H), 1.44-1.33 (m, 2H), 0.67 (t, 3H, J=7.4 Hz)

Example 31

4-(4-Fluorophenyl)-2-(4-methylthio)benzylthio-1-n-propyl-5-(4-pyridyl)-imidazole The title compound was prepared by the process of example 27, with n-propylamine being in step (a) and 4-methylthiobenzyl chloride being used in step (b) for the benzylation.

IR: $1/\lambda$ (cm$^{-1}$)=2922, 1602, 1508, 1405, 1222, 848, 814

$^1$H NMR (CDCl$_3$, ppm): 8.70-8.67 (m, 2H), 7.42-7.35 (m, 2H), 7.24-7.15 (m, 6H), 6.98-6.89 (m, 2H), 4.37 (s, 2H), 3.60 (t, 2H, J=7.6 Hz), 2.48 (s, 3H), 1.44-1.33 (m, 2H), 0.68 (t, 3H, J=7.4 Hz)

Example 32

4-(4-Fluorophenyl)-2-(4-methylsulfinyl)benzylthio-1-n-propyl-5-(4-pyridyl)imidazole The process of example 31 was repeated, except that in step (b) 4-methylsulfinyl-benzyl chloride was used for the benzylation.

IR: $1/\lambda$ (cm$^{-1}$)=2959, 1602, 1509, 1407, 1221, 1089, 1048, 842, 816

$^1$H NMR (CDCl$_3$, ppm): 8.71-8.68 (m, 2H), 7.63-7.51 (m, 4H), 7.41-7.34 (m, 2H), 7.21-7.18 (m, 2H), 6.98-6.90 (m, 2H), 4.48 (s, 2H), 3.64 (t, 2H, J=7.6 Hz), 2.72 (s, 3H), 1.42-1.35 (m, 2H), 0.69 (t, 3H, J=7.4 Hz)

Example 33

4-(4-Fluorophenyl)-2-(4-methylsulfonyl)benzylthio-1-n-propyl-5-(4-pyridyl)imidazole The process of example 31 was repeated, except that in step (b) 4-methylsulfonylbenzyl chloride was used for the benzylation.
IR: 1/λ (cm$^{-1}$)=1509, 1306, 1219, 1150, 964, 844, 768, 744
$^1$H NMR (CDCl$_3$, ppm): 8.70-8.68 (m, 2H), 7.91-7.87 (m, 2H), 7.62-7.58 (m, 2H), 7.41-7.26 (m, 4H), 7.0-6.92 (m, 2H), 4.55 (s, 2H), 3.66 (t, 2H, J=7.6 Hz), 3.05 (s, 3H), 1.48-1.37 (m, 2H), 0.71 (t, 3H, J=7.5 Hz)

Example 34

2-(4-Chlorobenzyl)thio-4-(4-fluorophenyl)-1-isopropyl-5-(4-pyridyl)-imidazole

The title compound was prepared by the process of example 27, where isopropylamine was used in step (a) and 4-chlorobenzyl chloride was used in step (b) for the benzylation.
IR: 1/λ (cm$^{-1}$)=1509, 1222, 1092, 850, 815
$^1$H NMR (CDCl$_3$, ppm): 8.73-8.71 (m, 2H), 7.38-7.21 (m, 8H), 6.97-6.88 (m, 2H), 4.49 (s, 2H), 4.27-4.20 (m, 1H), 1.38 (s, 3H), 1.27 (s, 3H)

Example 35

4-(4-Fluorophenyl)-2-(4-methylsulfonyl)benzylthio-1-isopropyl-5-(4-pyridyl)imidazole The title compound was prepared by the process from example 27, where isopropylamine was used in step (a) and 4-methylsulfonylbenzyl chloride was used in step (b) for the benzylation.
IR: 1/λ (cm$^{-1}$)=1510, 1306, 1219, 1149, 843, 766, 744
$^1$H NMR (CDCl$_3$, ppm): 8.72-8.69 (m, 2H), 7.92-7.88 (m, 2H), 7.67-7.62 (m, 2H), 7.35-7.21 (m, 4H), 4.60 (s, 2H), 4.25-4.18 (m, 1H), 3.05 (s, 3H), 1.39, 1.35 (2s, 6H)

Example 36

1-Cyclopropyl-4-(4-fluorophenyl)-2-(1-phenylpropynyl)thio-5-(4-pyridyl)-imidazole The title compound was prepared by the process of example 28, where 1,3,5-tricyclopropylhexahydro-1,3,5-triazine was used in step (a) and 1-phenylprop-1-ynyl chloride was used in step (b) for the benzylation.
IR: 1/λ (cm$^{-1}$)=1603, 1509, 1388, 1221, 842, 816, 753, 688
$^1$H NMR (CDCl$_3$, ppm): 8.64-8.61 (m, 2H), 7.44-7.22 (m, 9H), 6.99-6.91 (m, 2H), 4.31 (s, 2H), 3.18-3.11 (m, 1H), 0.97-0.90 (m, 2H), 0.75-0.69 (m, 2H)

Example 37

1-Cyclopropyl-4-(4-fluorophenyl)-2-(1-(4-chloro)phenylpropenyl)thio-5-(4-pyridyl)imidazole The procedure of example 36 was adopted, except that in step (b) 1-(4-chloro-phenyl)prop-1-enyl chloride was used for the benzylation.
$^1$H NMR (CDCl$_3$, ppm): 8.64-8.61 (m, 2H), 7.42-7.35 (m, 2H), 7.29-7.26 (m, 4H), 7.23-7.20 (m, 2H), 7.0-6.91 (m, 2H), 6.60 (d, 1H, J=15.7 Hz), 6.48-6.37 (m, 1H), 4.11 (d, 2H, J=6.5 Hz), 3.12-3.0 (m, 1H), 0.94-0.90 (m, 2H), 0.68-0.64 (m, 2H)

Example 38

1-Cyclopropyl-4-phenyl-2-(1-(4-fluorophenylpropenyl)thio-5-(4-pyridyl)-imidazole The procedure of example 36 was adopted, except that in step (b) 1-phenylprop-1-enyl chloride was used for the benzylation.
IR: 1/λ (cm$^{-1}$)=3025, 1599, 1509, 1384, 1219, 963, 838, 824, 815, 750, 692
$^1$H NMR (CDCl$_3$, ppm): 8.64-8.61 (m, 2H), 7.44-7.28 (m, 7H), 7.23-7.20 (m, 2H), 7.02-6.92 (m, 2H), 6.65 (d, 2H, J=15.8 Hz), 6.51-6.40 (m, 1H), 4.13 (d, 2H, J=6.7 Hz), 3.11-3.04 (m, 1H), 0.95-0.88 (m, 2H), 0.71-0.65 (m, 2H)

Example 39

1-Cyclohexyl-4-(4-fluorophenyl)-2-(4-methylsulfonyl)benzylthio-5-(4-pyridyl)imidazole The title compound was prepared by the process of example 27 where cyclo-hexylamine was used in step (a) and 4-methylsulfonylbenzyl chloride was used in step (b) for the benzylation.
IR: 1/λ (cm$^{-1}$)=2930, 1599, 1509, 1304, 1149, 838, 763
$^1$H NMR (CDCl$_3$, ppm): 8.73-8.70 (m, 2H), 7.92-7.88 (m, 2H), 7.67-7.63 (m, 2H), 7.34-7.21 (m, 4H), 6.97-6.88 (m, 2H), 4.64 (s, 2H), 3.73-3.71 (m, 1H), 2.10-1.62 (m, 10H)

Example 40

4-(4-Fluorophenyl)-2-(4-methylsulfonyl)benzylthio-1-phenyl-5-(4-pyridyl)imidazole The procedure of example 39 was adopted, except that the amine in step (a) was aniline.
IR: 1/λ (cm$^{-1}$)=1598, 1510, 1408, 1303, 1149, 1090, 840, 765, 694
$^1$H NMR (CDCl$_3$, ppm): 8.41-8.38 (m, 2H), 7.89-7.85 (m, 2H), 7.61-7.38 (m, 7H), 7.07-6.92 (m, 6H), 4.50 (s, 2H), 3.04 (s, 3H)

Example 41

1-Benzyl-4-(4-fluorophenyl)-2-(4-methylsulfonyl)benzylthio-5-(4-pyridyl)-imidazole The procedure of example 39 was adopted, except that the imine used in step (a) was benzylamine.
IR: 1/λ (cm$^{-1}$)=1600, 1509, 1304, 1220, 1147, 1090, 843, 767, 725
$^1$H NMR (CDCl$_3$, ppm): 8.57-8.54 (m, 2H), 7.90-7.85 (m, 2H), 7.58-7.54 (m, 2H), 7.45-7.38 (m, 2H), 7.26-7.23 (m, 3H), 7.08-6.97 (m, 4H), 6.80-6.79 (m, 2H), 4.93 (s, 2H), 4.47 (s, 2H), 3.05 (s, 3H)

Example 42

2-Benzylthio-4-(4-fluorophenyl)-1-N-morpholinoethyl-5-(4-pyridyl)-imidazole

The title compound was prepared by the process of example 27, where N-morpholinoethylamine was used in step (a) and benzyl chloride was used in step (b) for the benzylation.

IR: $1/\lambda$ (cm$^{-1}$)=2802, 1603, 1510, 1219, 1116, 870, 836, 814, 712, 695

$^1$H NMR (CDCl$_3$, ppm): 8.71-8.68 (m, 2H), 7.44-7.37 (m, 2H), 7.30-7.26 (m, 5H), 7.26-7.19 (m, 2H), 6.99-6.90 (m, 2H), 4.37 (s, 2H), 3.80-3.54 (m, 6H), 2.24-2.17 (m, 6H)

Example 43

2-Benzylthio-4-(4-fluorophenyl)-1-N-morpholinopropyl-5-(4-pyridyl-imidazole

Example 28 was repeated, except that the added imine compound in step (a) was 1,3,5-tri(3-N-morpholinopropyl)hexahydro-1,3,5-triazine.

IR: $1/\lambda$ (cm$^{-1}$)=2814, 1602, 1509, 1460, 1218, 1114, 970, 842, 812, 696

$^1$H NMR (CDCl$_3$, ppm): 8.70-8.67 (m, 2H), 7.43-7.26 (m, 7H), 7.20-7.17 (m, 2H), 6.98-6.89 (m, 2H), 4.39 (s, 2H), 3.74-3.56 (m, 6H), 2.19-2.06 (m, 6H), 1.55-1.36 (m, 2H)

Example 44

4-(4-Fluorophenyl)-2-(4-methylsulfonyl)benzylthio-1-N-morpholinoethyl-5-(4-pyridyl)imidazole

The title compound was prepared by the process of example 28, where 1,3,5-tri(3-N-morpholinopropyl)hexahydro-1,3,5-triazine was used in step (a) and 4-methyl-sulfonylbenzyl chloride was used in step (b) for the benzylation.

IR: $1/\lambda$ (cm$^{-1}$)=2924, 1600, 1510, 1302, 1147, 1115, 839, 765

$^1$H NMR (CDCl$_3$, ppm): 8.71-8.68 (m, 2H), 7.91-7.87 (m, 2H), 7.59-7.55 (m, 2H), 7.40-7.33 (m, 2H), 7.22-7.19 (m, 2H), 6.99-6.90 (m, 2H), 4.49 (s, 2H), 3.77 (t, 2H, J=5.7 Hz), 3.63-3.58 (m, 4H), 3.06 (s, 3H), 2.23-2.15 (m, 6H), 1.60-1.41 (m, 2H)

Example 45

4-(4-Fluorophenyl)-2-(4-methylsulfinyl)benzylthio-1-N-morpholinoethyl-5-(4-pyridyl)imidazole

The title compound was prepared by the process of example 28, where 1,3,5-tri(3-N-morpholinopropyl)hexahydro-1,3,5-triazine was used in step (a) and 4-methylsulfinylbenzyl chloride was used in step (b) for the benzylation.

IR: $1/\lambda$ (cm$^{-1}$)=2956, 1601, 1509, 1406, 1220, 1115, 1047, 837, 815

$^1$H NMR (CDCl$_3$, ppm): 8.71-8.68 (m, 2H), 7.63-7.50 (m, 4H), 7.41-7.34 (m, 2H), 7.22-7.19 (m, 2H), 6.98-90 (m, 2H), 4.47 (s, 2H), 3.78 (t, 2H, J=7.8 Hz), 3.60-3.56 (m, 4H), 2.73 (s, 3H), 2.20-2.09 (m, 6H), 1.60-1.42 (m, 2H)

Example 46

2-Benzylthio-4-(4-fluorophenyl)-1-(2,2,6,6-tetramethylpiperidin-4-yl)-imidazole

The title compound was prepared by the process of example 28, where 2,2,6,6-tetra-methyl-4-methylenaminopiperidine was used in step (a) and benzyl chloride was used in step (b) for the benzylation.

IR: $1/\lambda$ (cm$^{-1}$)=2739, 1602, 1510, 1390, 1354, 1224, 1158, 840, 700

Example 47

4-(4-Fluorophenyl)-1-methyl-2-N-morpholinoethylthio-5-(4-pyridyl-imidazole a) The 1-substituted 4-(4-fluorophenyl)-5-(4-pyridyl)imidazole-2-thione (compound 5 of scheme 1) was prepared as described in example 1, the added imine compound being 1,3,5-trimethylhexahydro-1,3,5-triazine.

b) To substitute the sulfur, 0.4 g of the resulting thione compound (5) was then suspended under protective gas in 20 ml of dry ethanol, and the equimolar amount of N-(2-chloroethyl)morpholine hydrochloride was added. A spatula tip of Na$_2$CO$_3$ and a spatula tip of NaI were added, and the reaction mixture was then heated under reflux for 5 h. After cooling, the salts were filtered off and the solvent was removed using a rotary evaporator. The crude product of the title compound (compound 10 of scheme 3) was purified by column chromatography.

Yield: 72%

IR: $1/\lambda$ (cm$^{-1}$)=2930, 2806, 1602, 1508, 1218, 1131, 1113, 1072, 1007, 865, 850, 829, 814

$^1$H NMR (CDCl$_3$, ppm): 8.70-8.67 (m, 2H), 7.41-7.34 (m, 2H), 7.26-7.21 (m, 2H), 6.97-6.88 (m, 2H), 3.69 (t, 4H, J=4.6 Hz), 3.50 (s, 3H), 3.39 (t, 3H, J=6.9 Hz), 2.79 (t, 2H, J=7.0 Hz), 2.52 (t, 4H, J=4.6 Hz)

Example 48

1-cis-Phenylethenylthio-4-(4-fluorophenyl)-1-methyl-5-(4-pyridyl)-imidazole a) The 1-substituted 4-(4-fluorophenyl)-5-(4-pyridyl)imidazole-2-thione (compound 5 of scheme 1) was prepared as described in example 1, the added imine compound being 1,3,5-trimethylhexahydro-1,3,5-triazine.

b) Dry ethanol was then added dropwise to an initial charge of 0.1 g of metallic sodium. 1.2 g of the compound (5) from step (a) were added, and a tenfold excess of phenylacetylene was then added. The reaction mixture was heated under reflux for 6 h. After cooling, the mixture was poured onto ice and extracted three times with petroleum ether. The organic phases were combined. When the organic phase was concentrated on a rotary evaporator, the title compound (compound 11 of scheme 3) precipitated out.

Yield: 27%

IR: $1/\lambda$ (cm$^{-1}$)=3380, 1600, 1513, 1226, 842

$^1$H NMR (CDCl$_3$, ppm): 8.72-8.69 (m, 2H), 7.52-7.23 (m, 9H), 6.99-6.90 (m, 3H), 6.74 (d, 1H, J=10.6 Hz), 3.52 (s, 3H)

Example 49

1-cis-Phenylethenylthio-4-(4-fluorophenyl)-1-n-propyl-5-(4-pyridyl)-imidazole

The title compound was prepared analogously to example 48, the imine added in step (a) being 1,3,5-tri-n-propyl-hexahydro-1,3,5-triazine.

IR: 1/λ (cm$^{-1}$)=1596, 1217, 835, 776, 682

$^1$H NMR (CDCl$_3$, ppm): 8.74-8.71 (m, 2H), 7.49-7.25 (m, 9H), 7.02-6.89 (m, 3H), 6.73 (d, 1H, J=10.7 Hz), 3.86 (t, 2H, J=7.7 Hz), 1.66-1.51 (m, 2H), 0.78 (t, 3H, J=7.4 Hz)

Example 50

2-cis-Phenylethenylthio-1-cyclopropyl-4-(4-fluorophenyl)-5-(4-pyridyl)-imidazole The title compound was prepared analogously to example 48, the imine added in step (a) being 1,3,5-tricyclopropyl-hexahydro-1,3,5-triazine.

IR: 1/λ (cm$^{-1}$)=1596, 1509, 1385, 1217, 832, 785, 686

$^1$H NMR (CDCl$_3$, ppm): 8.67-8.64 (m, 2H), 7.54-7.26 (m, 10H), 7.0-6.92 (m, 2H), 6.76 (d, 1H, J=10.8 Hz), 3.17-3.13 (m, 1H), 1.0-0.96 (m, 2H), 0.72-0.68 (m, 2H)

Example 51

2-(1,2-Dibromo-2-phenylethyl)thio-4-(4-fluorophenyl)-1-n-propyl-5-(4-pyridyl)imidazole To prepare the title compound, 0.4 g of the product of example 49 (compound 11 of scheme 3) was dissolved in CH$_2$Cl$_2$ and the equimolar amount of bromine in 15 ml of CH$_2$Cl$_2$ was slowly added dropwise. The reaction mixture was stirred at room temperature for 5 h and then washed repeatedly with aqueous sodium thiosulfate solution. The organic phase was dried over Na$_2$SO$_4$, the drying agent was filtered off and the solvent was removed using a rotary evaporator.

Yield: 98%

IR: 1/λ (cm$^{-1}$)=2963, 1631, 1603, 1513, 1224, 1158, 840, 815, 697

$^1$H NMR (CDCl$_3$, ppm): 8.74-8.72 (m, 2H), 7.59-7.25 (m, 9H), 6.99-6.90 (m, 2H), 6.21 (d, 1H, J=7.2 Hz), 5.74 (d, 1H, J=7.1 Hz), 3.89-3.85 (m, 2H), 1.55-1.51 (m, 2H), 0.77 (t, 3H, J=7.3 Hz)

Bisaryl Thioether

Example 52

4-(4-Fluorophenyl)-2-phenylthio-1-n-propyl-5-(4-pyridyl)imidazole

2-Chloro-1-n-propyl-4-(4-fluorophenyl)-5-(4-pyridyl)imidazole (compound 7 of scheme 4) was prepared analogously to the process described in example 2, the amine used being, as in example 3B, n-propylamine.

b) The resulting imidazole compound (7) was then converted into the bisaryl thioether. To this end, NaH (2 eq.) was suspended in 10 ml of dry DMF and thiophenol (2 eq.) was slowly added dropwise. The reaction mixture was stirred at room temperature for 45 min, and 0.3 g of (4) was then added. The mixture was heated under reflux for 5.5 h. After cooling, distilled water was added to the mixture, the pH was adjusted to 1 using concentrated HCl and the mixture was washed six times with diethyl ether. When the mixture was neutralized using 20% strength NaOH the title compound (compound 12 of scheme 4) precipitated out. The precipitate was filtered off and dried over P$_2$O$_5$ under reduced pressure.

Yield: 70%

IR: 1/λ (cm$^{-1}$)=1509, 1226, 847, 729, 685

$^1$H NMR (CDCl$_3$, ppm): 8.75-8.72 (m, 2H), 7.45-7.26 (m, 9H), 6.98-6.89 (m, 2H), 3.95-3.87 (m, 2H), 1.49-1.34 (m, 2H), 0.71 (t, 3H, J=7.4 Hz)

Example 53

2-(4-Chlorophenyl)thio-4-(4-fluorophenyl)-1-n-propyl-5-(4-pyridyl)-imidazole

The same process as in example 52 was carried out, except that in step (b) 4-chlorothiophenol was used.

IR: 1/λ (cm$^{-1}$)=2958, 1601, 1511, 1473, 1226, 1090, 1013, 854, 824

$^1$H NMR (d$_6$-DMSO, ppm): 8.74-8.71 (m, 2H), 7.49-7.32 (m, 8H), 7.14-7.05 (m, 2H), 3.92 (t, 2H, J=7.5 Hz), 1.37-1.26 (m, 2H), 0.59 (t, 3H, J=7.4 Hz)

Example 54

4-(4-Fluorophenyl)-2-(4-methylsulfanyl)phenylsulfanyl-1-n-propyl-5-(4-pyridyl)imidazole The same process as in example 52 was carried out, except that in step (b) 4-methylsulfanylthiophenol was used.

IR: 1/λ (cm$^{-1}$)=2961, 1602, 1510, 1478, 1226, 1103, 851, 796

$^1$H NMR (CDCl$_3$, ppm): 8.74-8.71 (m, 2H), 7.43-7.17 (m, 8H), 6.97-6.88 (m, 2H), 3.90 (t, 2H, J=7.7 Hz), 2.47 (s, 3H), 1.50-1.38 (m, 2H), 0.72 (t, 3H, J=7.4 Hz)

Example 55

4-(4-Fluorophenyl)-2-[(4-methylsulfinyl)phenyl]thio-1-n-propyl-5-(4-pyridyl)imidazole 0.4 g of the product of example 54 was dissolved in 10 ml of CH$_2$Cl$_2$ and 0.9 equivalent of m-chloroperbenzoic acid was added. The mixture was stirred at room temperature for 3 h. The resulting precipitate was filtered off and purified by column chromatography.

Yield: 73%

IR: 1/λ (cm$^{-1}$)=1602, 1510, 1226, 1056, 814, 699

$^1$H NMR (CDCl$_3$, ppm): 8.77-8.74 (m, 2H), 7.61-7.57 (m 2H), 7.46-7.37 (m, 4H), 7.30-7.28 (m, 2H), 6.98-6.90 (m, 2H), 3.92 (t, 2H, J=7.7 Hz), 2.72 (s, 3H), 1.49-1.45 (m, 2H), 0.72 (t, 3H, 7.4 Hz)

Example 56

4-(4-Fluorophenyl)-2-[(4-methylsulfonyl)phenyl]thio-1-n-propyl-5-(4-pyridyl)imidazole 0.4 g of the product of example 54 was dissolved in 10 ml of CH$_2$Cl$_2$ and 2.5 equivalents of m-chloroperbenzoic acid was added. The mixture was heated under reflux for 3 h. The resulting precipitate was filtered off and purified by column chromatography.

Yield: 67%

IR: 1/λ (cm$^{-1}$)=2967, 1604, 1510, 1316, 1226, 1153, 1094, 1078, 954, 815, 771

$^1$H NMR (CDCl$_3$, ppm): 8.79-8.76 (m, 2H), 7.88-7.83 (m, 2H), 7.45-7.27 (m, 6H), 6.99-6.90 (m, 2H), 3.92 (t, 2H, J=7.7 Hz), 3.04 (s, 3H), 1.50-1.43 (m, 2H), 0.73 (t, 3H, 7.4 Hz)

4-Methylimidazolethiols

Example 57

1-(4-Fluorophenyl)-4-methyl-5-(4-pyridyl)imidazole-2-thiol

The title compound was prepared analogously to example 1 from the corresponding α-hydroxyiminoethanone (compound 17 of scheme 6).

IR: 1/λ (cm$^{-1}$)=3039, 1591, 1516, 1372, 849, 823, 780
$^1$H NMR (d$_6$-DMSO, ppm): 12.76 (bs, 1H), 8.47-8.44 (m, 2H), 7.28-7.24 (m, 4H), 7.03-7.0 (m, 2H), 2.19 (s, 3H)

Example 58

4-(4-Fluorophenyl)-5-methyl-1-(3-pyridyl)imidazole-2-thiol

The title compound was prepared analogously to example 2 from the corresponding α-hydroxyiminoethanone (compound 19 of scheme 6).

IR: 1/λ (cm$^{-1}$)=3035, 1515, 1482, 1430, 1367, 1227, 844, 815, 711
$^1$H NMR (d$_6$-DMSO, ppm): 12.67 (bs, 1H), 8.50-8.49 (m, 1H), 8.48-8.47 (m, 1H), 7.69-7.65 (m, 1H), 7.45-7.41 (m, 1H), 7.16-7.12 (m, 4H), 2.08 (s, 3H)

Regioisomeric Thiols

Example 59

5-(4-Fluorophenyl)-1-n-propyl-4-(4-pyridyl)imidazole-2-thiol a) 1-(4-Fluorophenyl)-2-(4-pyridyl)-α-hydroxyiminoethanone 2.2 g (0.01 mol) of 1-(4-fluorophenyl)-2-(4-pyridyl)ethanone (compound 13 of scheme 5) were dissolved in 10 ml of glacial acetic acid. A solution of 0.7 g (0.01 mol) of NaNO$_2$ in 1 ml of water was slowly added dropwise to the initial charge, and the reaction mixture was stirred at room temperature for 2 h. 50 ml of distilled water were added and stirring was continued for 1 h. The precipitated compound (14), 1-(4-fluorophenyl)-2-(4-pyridyl)-α-hydroxyiminoethanone, was filtered off, washed with distilled water and dried over P$_2$O$_5$ under reduced pressure.

Yield: 2.0 g (80%)

b) 4-(4-Fluorophenyl)-1-methyl-5-(4-pyridyl)imidazole-2-thione 0.5 g of compound (14) was, together with twice the equivalent amount of 1,3,5-trimethylhexahydro-1,3,5-triazine, dissolved in 20 ml of dry ethanol and heated under reflux for 24 h. After cooling, the solvent was removed using a rotary evaporator. The residue was taken up in 20 ml of CHCl$_3$, cooled in an ice-bath, and 2,2,4,4-tetramethyl-3-thionocyclobutanone was slowly added with stirring. The ice-bath was removed and stirring was continued at room temperature for 1 h. The solvent was removed using a rotary evaporator and the resulting oily residue was solidified by addition of diethyl ether. The precipitate (15) was filtered off and purified by recrystallization.

Yield: 15%
IR: 1/λ (cm$^{-1}$)=2727, 1604, 1397, 1223, 833, 817
$^1$H NMR (CDCl$_3$, ppm): 12.03 (bs, 1H), 8.50-8.47 (m, 2H), 7.39-7.20 (m, 4H), 7.10-7.07 (m, 2H), 3.93-3.85 (m, 2H), 1.72-1.56 (m, 2H), 0.82 (t, 3H, J=7.4 Hz)

Example 60

5-(4-Fluorophenyl)-1-N-morpholinoethyl-4-(4-pyridyl)imidazole-2-thiol

The procedure of example 59 was adopted, except that the imine in step (b) was N-methylene-(N-morpholino)ethanamine.

IR: 1/λ (cm$^{-1}$)=2803, 1605, 1220, 1118, 849, 833
$^1$H NMR (d$_6$-DMSO): 13.09 (bs, 1H), 8.44-8.41 (m, 2H), 7.63-7.56 (m, 2H), 7.47-7.38 (m, 2H), 7.14-7.11 (m, 2H), 3.93 (t, 2H, J=6.8 Hz ), 3.44 (t, 4H, J=4.5 Hz), 2.42 (t, 2H, J=6.8 Hz), 2.14 (t, 4H, J=4.4 Hz)

Examples 61 to 65

(The compound numbers refer to scheme 8)

a) 2-Acetamido-4-methylpyridine (25)

100 mg of 4-dimethylaminopyridine are added to 200.0 g of 2-aminopicoline and 400 ml of acetic anhydride, and the mixture is refluxed for 5 h. After cooling, most of the excess acetic anhydride is distilled off, the residue is poured onto ice and the mixture is neutralized using aqueous ammonia solution. The resulting precipitate (25) is filtered off and dried under reduced pressure over P$_2$O$_5$.

Yield: 209.0 g (75%)

b) 2-Acetamidopyridine-4-carboxylic acid (26)

With stirring, 214.0 g of (25) are introduced a little at a time into an aqueous solution (temperature 50° C.) of 160 g of potassium permanganate. A further 360 g of potassium permanganate are added a little at a time over a period of one hour. Here, the temperature of the reaction mixture should not exceed 90° C. The mixture is stirred for another 1.5 h and then filtered hot, and the filtrate is adjusted to pH 3-4 using conc. HCl. The resulting white precipitate (26) is filtered off and dried under reduced pressure over P$_2$O$_5$.

Yield: 108.0 g (42%)

c) 2-Cyano-2-(4-fluorophenyl-1-(2-acetamido-4-pyridyl) ethanone (27)

18.0 g of (26) are taken up in 50 ml of abs. dimethylformamide (DMF), 17.0 g of carbonyldiimidazole (CDI) are added and the mixture is stirred at room temperature for 45 min. 14.9 g of 4-fluoroacetonitrile and 14.6 g of potassium tert-butoxide are then added, and the reaction mixture is heated at 120° C. for 2 h. After cooling, the mixture is stirred at room temperature overnight. Ice is then added to the solution, and the mixture is neutralized using conc. HCl. The resulting precipitate (27) is filtered off and dried under reduced pressure over P$_2$O$_5$.

Yield: 18.1 g (65%)

d) 2-(4-Fluorophenyl)-1-(2-amino-4-pyridyl)ethanone (28)

150 ml of 48% strength hydrobromic acid are added to 27.9 g of (27), and the reaction mixture is boiled gently for 30 h. After cooling, the mixture is poured onto ice and neutralized with concentrated ammonia. The resulting precipitate (28) is sucked dry, washed repeatedly with petroleum ether and cold diethyl ether and dried.

Yield: 11.7 g (55%)

e) 2-(4-Fluorophenyl)-1-(2-acetamido-4-pyridyl)ethanone (29)

12.0 g of the compound (28) are suspended in 100 ml of acetic anhydride, a spatula tip of 4-dimethylaminopyridine is added and the reaction mixture is heated under reflux for 5 h. Most of the excess acetic anhydride is distilled off, the residue is hydrolyzed and the mixture is adjusted to pH 7 using conc. ammonia. The resulting clear precipitate (29) is filtered off and dried under reduced pressure over $P_2O_5$.

Yield: 13.5 g (94%)

f) 2-(4-Fluorophenyl-1-(2-acetamido-4-pyridyl)-α-hydroxyiminoethanone (3)

30 ml of methanol are added to 2.1 g of sodium methoxide solution (30% in methanol), and this mixture is added to a solution of 1.2 g of isoamyl nitrite in 20 ml of methanol. With stirring, 3.0 g of (29) are added a little at a time, and the mixture is then stirred at room temperature for another 2 h. The solvent is distilled off, the solid residue is taken up in water and the pH is adjusted to 7 using 10% strength HCl. The resulting clear precipitate (30) is filtered off and dried under reduced pressure over $P_2O_5$.

Yield: 1.8 g (54%)

g) Preparation of the compounds (31):

(30) is, together with twice the amount of the appropriate triazine, dissolved in absolute ethanol and refluxed until the starting material has been completely converted. After cooling, the ethanol is removed using a rotary evaporator. The slightly oily residue solidifies on addition of diethyl ether. The precipitate of compounds 31 is filtered off and dried under reduced pressure.

Yields: R1=—$CH_3$: 74%
R1=—$C_3H_7$: 62%
R1=2,2,6,6-tetramethylpiperidin-4-yl: 81%
R1=N-morpholinopropyl-: 72%
R1=3-hydroxypropyl-: 56% h) Preparation of the compounds (32)

Compound (31) is dissolved in $CHCl_3$ and the reaction mixture is cooled in an ice-bath. An equimolar solution of 2,2,4,4-tetramethylcyclobutane-3-thioxobutanone in $CHCl_3$ is slowly added dropwise to the initial charge, and the mixture is then stirred in the ice-bath for 30 min. The ice-bath is removed and stirring is continued at room temperature for 1 h. The solvent is then removed using a rotary evaporator and the solid residue is triturated in diethyl ether. The precipitate (32) is filtered off and dried under reduced pressure.

Yields: R1=—$CH_3$: 96%
R1=—$C_3H_7$: 74%
R1=2,2,6,6-tetramethylpiperidin-4-yl: 61%
R1=N-morpholinopropyl-: 82%
R1=3-hydroxypropyl-: 71% i) Preparation of the Compounds (33)

Under protective gas, compound (32) is suspended in abs. ethanol, and an equimolar amount of methyl iodide is added. A spatula tip of $Na_2CO_3$ is added and the reaction mixture is refluxed until the starting material has been completely converted. After cooling, the inorganic salts are filtered off and the solvent is removed using a rotary evaporator. The crude product (33) is purified by column chromatography.

Example 61

4-(4-Fluorophenyl)-1-methyl-5-(2-acetamido-4-pyridyl)-2-methyl-thioimidazole

R1=—$CH_3$: Yield 63%
NMR ($CDCl_3$, ppm): 8.75 (bs, 1H), 8.26-8.24 (m, 2H), 7.46-7.39 (m, 2H), 6.97-6.88 (m, 3H), 3.53 (s, 3H), 2.71 (s, 3H), 2.23 (s, 3H)
IR (1/cm): 1669, 1607, 1543, 1505, 1416, 1268, 1218, 843

Example 62

4-(4-Fluorophenyl)-1-n-propyl-5-(2-acetamido-4-pyridyl)-2-methyl-thioimidazole

R1=—$C_3H_7$: Yield 28%
NMR ($CDCl_3$, ppm): 8.28-8.25 (m, 2H), 7.44-7.37 (m, 2H), 6.96-6.88 (m, 2H), 3.85 (t, 2H, J=7.7 Hz), 2.73 (s, 3H), 2.24 (s, 3H), 1.65-1.57 (m, 2H), 0.83 (t, 3H, J=7.4 Hz)
IR (1/cm): 3303, 1674, 1544, 1501, 1416, 1264, 1213, 845

Example 63

4-(4-Fluorophenyl)-1-(2,2,6,6-tetramethylpiperidin-4-yl)-5-(2-acetamido-4-pyridyl)-2-methylthioimidazole R1=2,2,6,6-tetramethylpiperidin-4-yl: Yield 23%
NMR ($CDCl_3$, ppm): 10.62 (s, 1H), 8.38-8.35 (m, 2H), 8.01 (s, 1H), 7.33-7.26 (m, 2H), 7.04-6.95 (m, 3H), 4.19-4.03 (m, 1H), 2.61 (s, 3H), 2.00 (s, 3H), 1.87-1.81 (m, 2H), 1.52-1.47 (m, 2H), 0.93 (s, 6H), 0.78 (s, 6H)
IR (1/cm): 2976, 1699, 1533, 1407, 1255, 838

Example 64

4-(4-Fluorophenyl)-1-[3-(N-morpholino)propyl]-5-(2-acetamido-4-pyridyl)-2-methylthioimdazole R1=N-morpholinopropyl-: Yield 52%
NMR ($CDCl_3$, ppm): 8.29 (m, 1H), 8.12 (s, 1H), 7.42-7.35 (m, 2H), 6.96-6.87 (m, 3H), 4.08-3.92 (m, 6H), 3.17-3.00 (m, 6H), 2.74 (s, 3H), 2.41-2.34 (m, 2H), 2.24 (s, 3H)

Example 65

4-(4-Fluorophenyl)-1-(3-hydroxypropyl)-5-(2-acetamido-4-pyridyl)-2-methylthioimidazole R1=3-hydroxypropyl-: Yield 32%
NMR ($CDCl_3$, ppm): 8.69 (bs, 1H), 8.23-8.19 (m, 2H), 7.44-7.37 (m, 2H), 6.98-6.86 (m, 3H), 4.04 (t, 2H, J=7.9 Hz), 3.70 (t, 2H, J=7.2 Hz), 2.74 (s, 3H), 2.25 (s, 3H), 2.13-2.05 (m, 2H)

Example 66

4-(4-Fluorophenyl)-1-methyl-5-(2-amino-4-pyridyl)-2-methyl-thioimidazole

The compound of example 61 is dissolved in 10% strength HCl and refluxed for 14 h. After cooling, the mixture is neutralized with 20% strength NaOH. The resulting clear precipitate is filtered off and dried under reduced pressure over $P_2O_5$.

Yield: 82%
NMR ($CDCl_3$, ppm): 8.16-8.13 (m, 1H), 7.50-7.43 (m, 2H), 6.98-6.89 (m, 2H), 6.60-6.57 (m, 1H), 6.41 (s 1H), 4.60 (bs, 2H,) 3.46 (s, 3H), 2.70 (s, 3H)
IR (1/cm): 1629, 1542, 1509, 1215, 837, 814

Examples 67 to 69

The compound of example 66 is dissolved in abs. tetrahydrofuran (THF), and 1.2 times the amount of triethylamine is added. The reaction mixture is cooled in an ice-bath. With stirring, 1.2 times the amount of the acid chloride is added dropwise, and stirring is continued until no more starting material is present. The reaction mixture is filtered and the filtrate is concentrated to dryness. Purification of the crude product is carried out by column chromatography.

Example 67

4-([lacuna]-Fluorophenyl)-1-methyl-5-[2-(4-methoxybenzamido)-4-pyridyl]-2-methylthioimidazole Yield: 62%
NMR (CDCl$_3$, ppm): 8.66 (s, 1H), 8.44 (s, 1H), 8.30 (s, 1H), 8.29-8.28 (m, 1H), 7.94-7.89 (m, 2H), 7.49-7.42 (m, 2H), 6.95-6.90 (m, 4H), 3.90 (s, 3H), 3.58 (s, 3H), 2.72 (s, 3H)
IR (1/cm): 3410, 1674, 1500, 1412, 1253, 1175, 840, 759

Example 68

4-([lacuna]-Fluorophenyl)-1-methyl-5-(2-cyclopropylamido-4-pyridyl)-2-methylthioimidazole Yield: 24%
NMR (CDCl$_3$, ppm): 8.67-8.62 (m, 1H), 7.63-7.38 (m, 3H), 6.98-6.85 (m, 3H), 3.90 (s, 3H), 2.73 (s, 3H), 2.05-1.98 (m, 1H), 1.26-1.14 (m, 2H), 1.21-1.14 (m, 2H)

Example 69

4-([lacuna]-Fluorophenyl)-1-methyl-5-(2-cyclopentylamido-4-pyridyl)-2-methylthioimidazole Yield: 53%
NMR (CDCl$_3$, ppm): 8.28-8.22 (m, 3H), 7.46-7.39 (m, 2H), 6.97-6.87 (m, 3H), 3.54 (s, 3H), 2.69 (s, 3H), 1.97-1.67 (m, 8H)

Examples 70 to 72

1.2 eq. of NaH are suspended in DMF, the compound of example 66 is added slowly and the reaction mixture is stirred at room temperature for 1 h. An equimolar amount of the benzyl bromide or phenylethyl bromide is added and the mixture is refluxed until no more starting material is present. The reaction mixture is diluted with water and the resulting precipitate is filtered off. The crude product is purified by column chromatography.

Example 70

4-(4-Fluorophenyl)-1-methyl-5-(2-benzylamino-4-pyridyl)-2-methyl-thioimidazole

Yield: 13%
NMR (CDCl$_3$, ppm): 8.12-8.16 (m, 1H), 7.47-7.26 (m, 7H), 6.95-6.86 (m, 2H), 6.53-6.50 (m, 1H), 6.24 (s, 1H), 5.30 (bs, 1H), 4.47 (d, 2H, J=5.8 Hz), 3.32 (s, 3H), 2.68 (s, 3H)
IR (1/cm): 3241, 1610, 1507, 1219, 839, 813, 737, 698

Example 71

4-(4-Fluorophenyl)-1-methyl-5-[2-(2-phenylethyl)amino-4-pyridyl]-2-methylthioimidazole Yield: 54%
NMR (CDCl$_3$, ppm): 8.12-8.10 (m, 1H), 7.41-7.19 (m, 7H), 6.92-6.84 (m, 2H), 6.46-6.43 (m, 1H), 6.06 (s, 1H), 5.18 (d, 1H, J=6.3 Hz), 4.63-4.57 (m, 1H), 3.11 (s, 3H), 2.70 (s, 3H),
IR (1/cm): 1605, 1505, 1432, 1219, 839, 701

If 2.5 times the amount of benzyl bromide is added, the nitrogen (13) is disubstituted.

Example 72

4-(4-Fluorophenyl)-1-methyl-5-(2-dibenzylamino-4-pyridyl)-2-methyl-thioimidazole Yield: 81%
NMR (CDCl$_3$, ppm): 8.27-8.24 (m, 1H), 7.45-7.19 (m, 12H), 6.95-6.86 (m, 2H), 6.51-6.48 (m, 1H), 6.31 (s, 1H), 4.80 (s, 4H), 3.17 (s, 3H), 2.66 (s, 3H)
IR (1/cm): 1598, 1496, 1427, 1219, 840, 831, 734, 702

Examples 73 to 75

The compound of examples 61, 62 or 63 is dissolved in THF and, with stirring, a 10-fold excess of LiAlH$_4$ is added. The reaction mixture is then heated for 2 h. After cooling, water is added slowly. The mixture is extracted repeatedly with CH$_2$Cl$_2$ and the combined organic phases are dried over Na$_2$SO$_4$. The drying agent is filtered off and the solvent is removed. The crude product is purified by column chromatography.

Example 73

4-(4-Fluorophenyl-1-methyl-5-(2-ethylamino-4-pyridyl)-2-methyl-thioimidazole

Yield: 70%
NMR (CDCl$_3$, ppm): 8.17-8.15 (m, 1H), 7.53-7.46 (m, 2H), 6.98-6.89 (m, 2H), 6.52-6.49 (m, 1H), 6.27-6.26 (m, 1H), 4.59 (t, 1H, J=6.0 Hz), 3.47 (s, 3H), 3.29-3.23 (m, 2H), 2.70 (s, 3H), 1.23 (t, 3H, J=7.1 Hz)
IR (1/cm): 3235, 1604, 1562, 1506, 1435, 1221, 844, 806

Example 74

4-(4-Fluorophenyl)-1-n-propyl-5-(2-ethylamino-4-pyridyl)-2-methylthioimidazole

Yield: 25%
NMR (CDCl$_3$, ppm): 8.17-8.14 (m, 1H), 7.51-7.43 (m, 2H), 6.98-6.87 (m, 2H), 6.53-6.50 (m, 1H), 6.27 (s, 1H), 4.61 (t, 1H, J=2.8 Hz), 3.79 (t, 2H, 7.7 Hz), 3.28-3.22 (m, 2H), 2.71 (s, 3H), 1.66-1.54 (m, 2H), 1.24 (t, 3H, J=7.2 Hz), 0.83 (t, 3H, J=7.4 Hz)
IR (1/cm): 3275, 2930, 1607, 1525, 1507, 1219, 846, 813

Example 75

4-(4-Fluorophenyl)-1-(2,2,6,6-tetramethylpiperidin-4-yl-5)-2-ethylamino-4-pyridyl)-2-methylthioimidazole Yield: 52%
NMR (CDCl$_3$, ppm): 8.10-8.07 (m, 2H), 7.47-7.40 (m, 2H), 7.12-7.03 (m, 2H), 6.44-6.41 (m, 1H), 6.37 (s, 1H), 4.30-4.14 (m, 1H), 3.27-3.21 (m, 2H), 2.66 (s, 3H), 2.11-1.91 (m, 2H), 1.59-1.52 (m, 2H), 1.12-1.01 (m, 9H), 0.90 (s, 6H)

IR (1/cm): 3325, 2959, 1603, 1516, 1499, 1217, 1158, 849, 812

Example 76

4-(4-Fluorophenyl)-1-(3-N-morpholinopropyl)-5-(2-acetamido-4-pyridyl)-2-(4-methylsulfinylbenzyl)thioimidazole Under protective gas, 4-(4-fluorophenyl)-1-(3-N-morpholinopropyl)-5-(2-acetamido-4-pyridyl)imidazole-2-thione is suspended in abs. ethanol and an equimolar amount of 4-methylsulfinylbenzyl chloride is added. A spatula tip of $Na_2CO_3$ is added and the reaction mixture is then refluxed until the starting material has been converted completely. After cooling, the inorganic salts are filtered off and the solvent is removed using a rotary evaporator. The crude product is purified by column chromatograpy.

Yield: 27%

NMR ($CDCl_3$, ppm): 8.67 (bs, 1H), 8.28-8.25 (m, 2H), 8.12 (s, 1H), 7.64-7.49 (m, 4H), 7.44-7.37 (m, 2H), 6.98-6.86 (m, 3H), 4.45 (s, 2H), 3.81-3.65 (m, 6H), 2.72 (s,3H), 2.54-2.52 (m, 6H), 2.22 (s, 3H), 1.85-1.73 (m, 2)

Using the process described above, the following compounds were obtained:

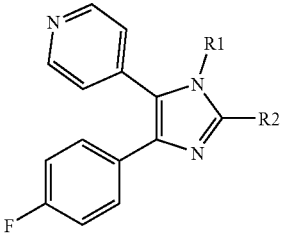

| Example | $R^1$ | $R^2$ |
|---|---|---|
| 77 | cyclo-$C_6H_{11}$ | $CH_3$ |
| 78 | —$(CH_2)_2$—$N(CH_3)_2$ | $CH_3$ |
| 79 | —$(CH_2)_3$—OH | $CH_3$ |
| 80 | —$(CH_2)_3$—$OCH_3$ | $CH_3$ |
| 81 | $CH_3$ | —$(CH_2)_2$ S $CH_3$ |
| 82 | $CH_3$ | —$(CH_2)_2$ SO $CH_3$ |
| 83 | cyclo-$C_6H_{11}$ | $CH_2$-Ph-4-SO $CH_3$ |
| 84 | cyclo-$C_6H_{11}$ | $CH_2$-Ph-4-$SCH_3$ |

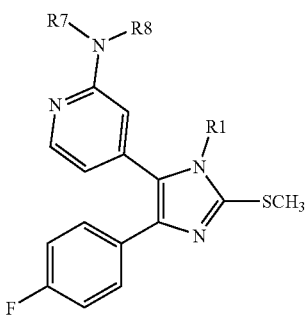

| Example | R1 | R7 | R8 |
|---|---|---|---|
| 85 | 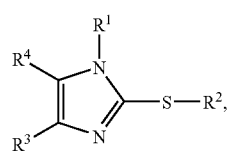 | $COCH_3$ | H |
| 86 | (similar piperidine structure) | $C_2H_5$ | H |
| 87 | n-$C_3H_7$ | H | H |
| 88 | $CH_3$ | benzyl | benzyl |

The invention claimed is:

1. A 2-thio-substituted imidazole derivative of the formula I $$\text{(I)}$$

(structure with $R^1$, $R^2$, $R^3$, $R^4$ substituents on imidazole with S—$R^2$)

wherein $R^1$ is selected from the group consisting of:
$C_1$-$C_6$-alkyl which is unsubstituted or substituted by one or two hydroxyl or $C_1$-$C_4$-alkoxy groups or by a nonaromatic heterocyclic radical having 5 or 6 ring atoms and 1 or 2 heteroatoms independently of one another selected from the group consisting of N, O and S, $C_2$-$C_6$-alkenyl, $C_3$-$C_6$-cycloalkyl, aryl which is unsubstituted or substituted by one or more halogen atoms or by a $C_1$-$C_4$-alkylsulfanyl group, amino-$C_1$-$C_4$-alkyl, where the amino group is unsubstituted or substituted by one or two $C_1$-$C_4$-alkyl groups, aminoaryl, where the amino group is unsubstituted or substituted by one or two $C_1$-$C_4$-alkyl groups, aryl-$C_1$-$C_4$-alkyl and an aromatic or nonaromatic heterocyclic radical having 5 or 6 ring atoms and 1 or 2 heteroatoms independently of one another selected from the group consisting of N, O and S, which heterocyclic radical is unsubstituted or substituted by 1, 2, 3 or 4 $C_1$-$C_4$-alkyl groups, an aryl or aryl-$C_1$-$C_4$-alkyl group, $R^2$ is selected from the group consisting of:

$C_1$-$C_6$-alkyl, phenyl-$C_1$-$C_4$-alkyl, where the phenyl group may have one or two substituents independently of one another selected from the group consisting of $C_1$-$C_4$-alkyl, halogen, $C_1$-$C_4$-alkylsulfanyl, $C_1$-$C_4$-alkylsulfinyl and $C_1$-$C_4$-alkylsulfonyl, $C_2$-$C_6$-alkenyl, $C_2$-$C_6$-alkenyl which is substituted by one or two halogen atoms and/or phenyl groups, where the phenyl group may independently be substituted by one or two $C_1$-$C_4$-alkyl or halogen atoms, $C_2$-$C_6$-alkynyl, $C_2$-$C_6$-alkynyl which is substituted by a phenyl group which may be unsubstituted or substituted by one or two $C_1$-$C_4$-alkyl or halogen atoms, $C_1$-$C_6$-alkyl which is substituted by a nonaromatic heterocyclic radical having 5 or 6 ring atoms and 1 or 2 heteroatoms independently of one another selected from the group consisting of N, O and S, $C_1$-$C_4$-alkylsulfanyl, $C_1$-$C_4$-alkylsulfinyl or $C_1$-$C_4$-alkylsulfonyl, phenyl and phenyl which has one or two substituents independently of one another selected from the group consisting of $C_1$-$C_4$-alkyl, halogen, $C_1$-$C_4$-alkylsulfanyl, $C_1$-$C_4$-alkylsulfinyl and $C_1$-$C_4$-alkylsulfonyl, or $R^1$ and $R^2$ together are —$CH_2CH_2$— or —$CH_2CH_2CH_2$—, $R^3$ is halogen substituted phenyl, $R^4$ is 4-pyridyl which is substituted by amino, $C_1$-$C_4$-alkylamino, phenyl-$C_1$-$C_4$-alkylamino or $R^5CONR^6$—, where $R^5$ is $C_1$-$C_4$-alkyl, phenyl, which may have one or two substituents independently of one another selected from the group consisting of $C_1$-$C_4$-alkyl, $C_1$-$C_4$-alkoxy and halogen, or $C_3$-$C_6$-cycloalkyl and $R^6$ is H, $C_1$-$C_4$-alkyl or benzyl, and with the proviso that, if $R^1$ represents aryl-$C_1$-$C_5$-alkyl or amino-$C_1$-$C_6$-alkyl, where the amino group is unsubstituted or substituted by one or two $C_1$-$C_4$-alkyl groups, $R^2$ represents alkylsulfonyl- or alkylsulfinylaryl-$C_1$-$C_5$-alkyl, or an optical isomer or physiologically acceptable salt thereof.

2. A compound as claimed in claim 1, wherein the pyridyl is substituted in 2-position.

3. A compound as claimed in claim 1, wherein $R^4$ is 4-pyridyl which is substituted by phenyl-$C_1$-$C_4$-alkylamino.

4. A compound as claimed in claim 1, wherein $R^3$ is 4-fluorophenyl.

5. A compound of the formula I as claimed in claim 1, wherein $R^1$ is $C_1$-$C_3$-alkyl, $C_3$-$C_6$-cycloalkyl or 2,2,6,6-tetramethylpiperidinyl.

6. A compound as claimed in claim 5, wherein $R^1$ is $C_1$-$C_3$-alkyl or 2,2,6,6-tetramethylpiperidinyl.

7. A compound of the formula I as claimed in claim 1, wherein $R^2$ is $C_1$-$C_6$-alkyl or phenyl-$C_1$-$C_4$-alkyl, where the phenyl group is substituted by $C_1$-$C_4$-alkylsulfanyl, $C_1$-$C_4$-alkylsulfinyl or $C_1$-$C_4$-alkylsulfonyl.

8. A compound of the formula I as claimed in claim 1, wherein $R^1$ is $C_1$-$C_6$-alkyl which is unsubstituted or substituted by one or two hydroxyl or $C_1$-$C_4$-alkoxy groups, or a nonaromatic heterocyclic radical having 5 or 6 ring atoms and 1 or 2 heteroatoms independently of one another selected from the group consisting of N, O and S, $C_3$-$C_6$-cycloalkyl or an aromatic or nonaromatic heterocyclic radical having 5 or 6 ring atoms and 1 or 2 heteroatoms independently of one another selected from the group consisting of N, O and S, which heterocyclic radical is unsubstituted or substituted by 1, 2, 3 or 4 $C_1$-$C_4$-alkyl groups, an aryl or aryl-$C_1$-$C_4$-alkyl group, $R^2$ is, $C_1$-$C_6$-alkyl, phenyl-$C_1$-$C_4$-alkyl, where the phenyl group may have one or two substituents independently of one another selected from the group consisting of $C_1$-$C_4$-alkyl, halogen, $C_1$-$C_4$-alkylsulfanyl, $C_1$-$C_4$-alkylsulfinyl and $C_1$-$C_4$-alkylsulfonyl, phenyl, $C_1$-$C_6$-alkyl substituted by a nonaromatic heterocyclic radical having 5 or 6 ring atoms and 1 or 2 heteroatoms independently of one another selected from the group consisting of N, O and S, $C_1$-$C_4$-alkylsulfanyl, $C_1$-$C_4$-alkylsulfinyl or $C_1$-$C_4$-alkylsulfonyl, or is phenyl which has one or two substituents independently of one another selected from the group consisting of $C_1$-$C_4$-alkyl, halogen, $C_1$-$C_4$-alkylsulfanyl, $C_1$-$C_4$-alkylsulfinyl and $C_1$-$C_4$-alkylsulfonyl, $R^1$ and $R^2$ together are —$CH_2CH_2$— or —$CH_2CH_2CH_2$—, $R^3$ is halogen substituted phenyl, and $R^4$ is 4-pyridyl which is substituted by amino, $C_1$-$C_4$-alkylamino, phenyl-$C_1$-$C_4$-alkylamino or $R^5CONR^6$—, where $R^5$ is $C_1$-$C_4$-alkyl, phenyl which may have one or two substituents independently of one another selected from the group consisting of $C_1$-$C_4$-alkyl, $C_1$-$C_4$-alkoxy and halogen, or $C_3$-$C_6$-cycloalkyl and $R^6$ is H, $C_1$-$C_4$-alkyl or benzyl, or an optical isomer or physiologically acceptable salt thereof.

9. A compound as claimed in claim 8, wherein $R^1$ is $C_1$-$C_3$-alkyl, $C_3$-$C_6$-cycloalkyl or 2,2,6,6-tetramethylpiperidinyl.

10. A compound as claimed in claim 8, wherein $R^2$ is $C_1$-$C_6$-alkyl or phenyl-$C_1$-$C_4$-alkyl, where the phenyl group is substituted by $C_1$-$C_4$-alkylsulfanyl, $C_1$-$C_4$-alkylsulfinyl or $C_1$-$C_4$-alkylsulfonyl.

11. A compound as claimed in claim 8, wherein $R^4$ is 4-pyridyl which is substituted by phenyl-$C_1$-$C_4$-alkylamino.

12. A pharmaceutical composition, comprising at least one compound as claimed in claim 1, together with one or more pharmaceutically acceptable carriers and/or additives.

* * * * *